(12) United States Patent
Beard et al.

(10) Patent No.: US 7,728,014 B2
(45) Date of Patent: Jun. 1, 2010

(54) HETEROAROMATIC COMPOUNDS HAVING SPHINGOSINE-1-PHOSPHATE (S1P) RECEPTOR AGONIST BIOLOGICAL ACTIVITY

(75) Inventors: Richard L. Beard, Newport Beach, CA (US); John E. Donello, Dana Point, CA (US); Haiqing Yuan, Irvine, CA (US); Xiaoxia Liu, Lake Forest, CA (US)

(73) Assignee: Allergan, Inc., Irvine ( * ) Notice: Subject to any disclaimer, the term of this patent is extended or adjusted under 35 U.S.C. 154(b) by 0 days.

(21) Appl. No.: 11/850,756

(22) Filed: Sep. 6, 2007

(65) Prior Publication Data
US 2008/0064872 A1 Mar. 13, 2008

Related U.S. Application Data

(60) Provisional application No. 60/824,805, filed on Sep. 7, 2006, provisional application No. 60/824,807, filed on Sep. 7, 2006.

(51) Int. Cl.
C07D 213/04 (2006.01)
A61K 31/44 (2006.01)
A61P 37/00 (2006.01)
A61P 31/00 (2006.01)

(52) U.S. Cl. .................................. 514/345; 546/261
(58) Field of Classification Search ................ 546/261; 514/345
See application file for complete search history.

(56) References Cited

U.S. PATENT DOCUMENTS 6,509,469 B1 * 1/2003 Shintou et al. ............. 546/252
7,271,266 B2 * 9/2007 Finke et al. ................ 546/336

FOREIGN PATENT DOCUMENTS

WO  WO-03/084930 A1 * 10/2003
WO  WO2005/058848    6/2005

OTHER PUBLICATIONS

Hughes et al., Journal of American Chemical Society, 127(44), 15644-15651 and supplements S1-S138.*
Gilchrist et al., Tetrahedron, 49(24), 5277-5290, 1993; CA 120: 106940, 1994.*
Dittmar et al., Tetrahedron Letters, 59, 5171-5174, 1969; CA 72: 78841, 1970.*
Francisco Palacios, et al., "Synthesis and Reactivity of Imines Derived from Bisphosphonates and 3-Phosphorylated 2-Aza-1,3-dienes," Tetrahedron vol. 56, No. 34 (2000), pp. 6319-6330.
Domitila Aparicio, et al., "straightforward Access to Pyrazines, Piperazinones, and Oquinoxalines by Reactions of 1,2-Diaza-1,3-butadienes with 1,2-Diamines under Solution, Solvent-Free, or Solid-Phase Conditions," J. Org. Chem. 2006, 71, pp. 5897-5905, XP-002466429.
Database Beilstein, XP002466430, 1995.
Database Beilstein, XP002466431, 1995.
Database Beilstein, XP002466432, 1955.
Database Beilstein, XP002466433, 1981.
Database Beilstein, XP002466434, 1956.
Database Beilstein, XP002466435, 2002.
Database accession No. 602026 Beilstein, XP002495008, 2004.
Database accession No. 2436778 Beilstein, XP002495009, 2002.
Database accession No. 4818030 Beilstein, XP002495010, 2005.
Database accession No. 2532400 Beilstein, XP002495011, 1977.
Database accession No. 4223051 Beilstein, XP002495012, 2005.
Database accession No. 2528516 Beilstein, XP002495013, 1977.
Database accession No. 602032 Beilstein, XP002495014, 1977.

* cited by examiner

*Primary Examiner*—Venkataraman Balasubramanian
(74) *Attorney, Agent, or Firm*—Kevin J. Forrestal; John E. Wurst; Allergan, Inc.

(57) ABSTRACT

A novel compound having agonist activity at the $S_1P_3$ receptor which is represented by the formula I

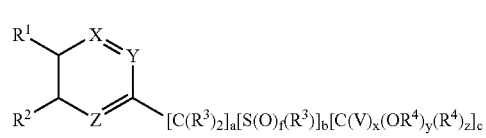

wherein
X is selected from the group consisting of $CR^3$, N and NO;
Y is selected from the group consisting of $CR^3$, N and NO;
Z is selected from the group consisting of $CR^3$, N and NO;
and at least one of X, Y and Z is N or NO;
V is O or $NOR^4$
$R^1$ is an aryl group;
$R^2$ is an aryl group;
$R^3$ is selected from the group consisting of H and alkyl; and 2 of said $R^3$ groups may together form a cyclic alkyl ring having from 3 to 6 carbon atoms;
$R^4$ is selected from the group consisting of H and alkyl;
a is 0 or an integer of from 1 to 6;
b is 0 or 1;
c is 0 or 1;
f is 0 or an integer of 1 or 2;
x is 0 or 1;
y is 0 or an integer of from 1 to 3; and
z is 0 or an integer of from 1 to 3.

7 Claims, No Drawings

HETEROAROMATIC COMPOUNDS HAVING SPHINGOSINE-1-PHOSPHATE (S1P) RECEPTOR AGONIST BIOLOGICAL ACTIVITY

RELATED APPLICATIONS

This application claims the benefit of U.S. Provisional Application Nos. 60/824,805 and 60/824,807, both filed on Sep. 7, 2006, each of which is hereby incorporated by reference in its entirety.

BACKGROUND OF THE INVENTION

1. Field of the Invention

The present invention relates to derivatives and/or analogues of sphingosine and pharmaceutical compositions, including such derivatives and/or analogues, which are useful as drugs for the treatment of fungal infections, allergic diseases, immune disorders, etc.

2. Summary of the Art

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

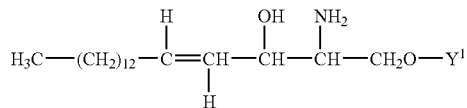

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 μM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

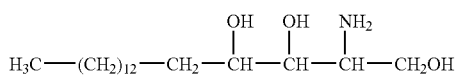

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683, 5,110, 987, 6,235,912 B1, 6,239,297 B1.

SUMMARY OF THE INVENTION

The present invention provides a derivative or analogue of sphingosine that is able to regulate the functions of sphingolipid, and pharmaceutical compositions comprising said derivative or analogue.

These compounds are represented by the formula I, which compounds have sphingosine-1-phosphate receptor agonist biological activity:

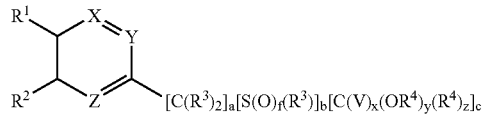

wherein
X is selected from the group consisting of $CR^3$, N and NO;
Y is selected from the group consisting of $CR^3$, N and NO;
Z is selected from the group consisting of $CR^3$, N and NO;
and at least one of X, Y and Z is N or NO;
V is O or $NOR^4$
$R^1$ is an aryl group;
$R^2$ is an aryl group;
$R^3$ is selected from the group consisting of H and alkyl; and 2 of said $R^3$ groups may together form a cyclic alkyl ring having from 3 to 6 carbon atoms;
$R^4$ is selected from the group consisting of H and alkyl;
a is 0 or an integer of from 1 to 6;
b is 0 or 1;
c is 0 or 1;
f is 0 or an integer of 1 or 2;
x is 0 or 1;
y is 0 or an integer of from 1 to 3; and
z is 0 or an integer of from 1 to 3.

Specific Examples of the compounds of formula I include

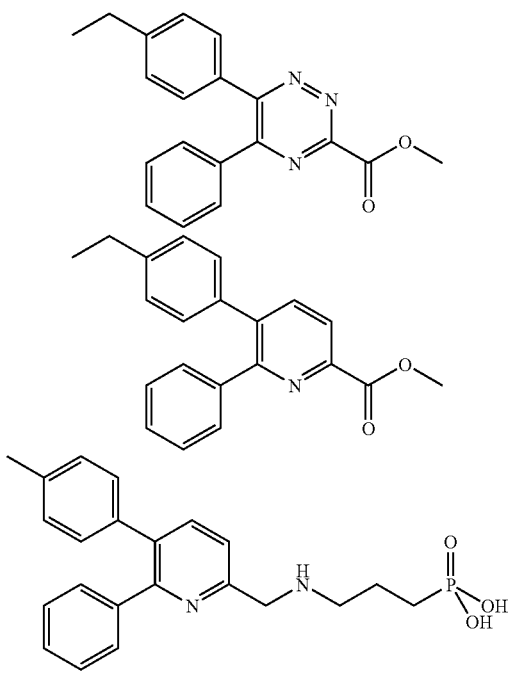

These compounds may be synthesized as illustrated by the synthesis scheme below:

It is noted that, in the general synthetic schemes used throughout this patent application, the various substituents designated as R, $R^1$, $R^2$ etc. may represent substituents which differ from the substituents that R, $R^1$, $R^2$ etc. represent in the above formula I. However, it will be apparent to the skilled artisan that it is intended for the definition of the invention, as claimed, that the definition of the substituents in formula I control in defining the scope of the invention, while the substituents of the general synthetic scheme are for the purpose of showing the making of the claimed compounds

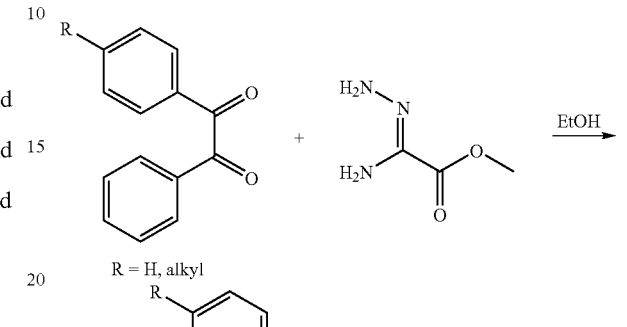

R = H, alkyl

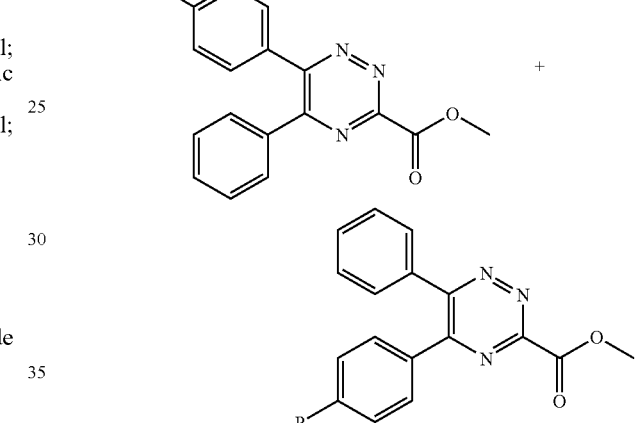

(1:1)
Seperated by MPLC

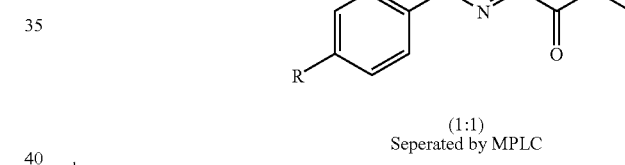

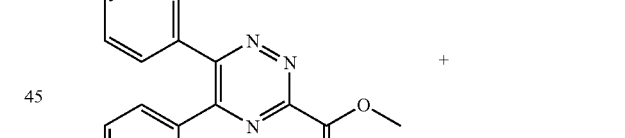

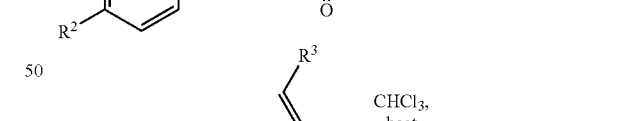

1) Dibal-H
2) NaCNBH$_3$, HOAc
Bu$_4$NOH

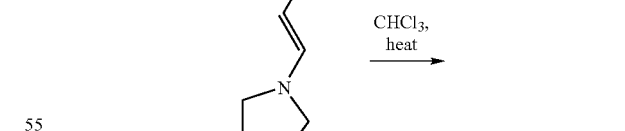

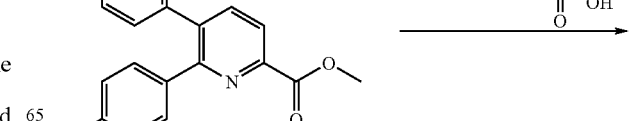

-continued

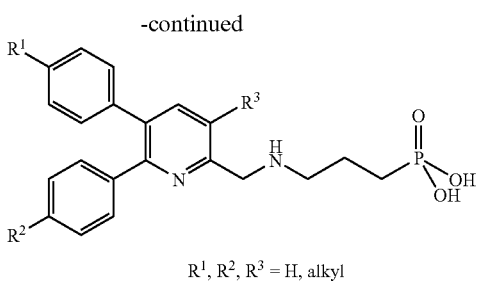

$R^1, R^2, R^3$ = H, alkyl

In general, a diphenylethyl-1,2-dione (e.g. benzil) is treated with methyl oxalamidrazonate in ethanol to produce a methyl 5,6-diphenyl-1,3,4-triazine-2-carboxylate (as a mixture of geometric isomers if the dione is asymmetrical). These triazines can undergo Diels-Aler reactions with a pyrrolidine enamine compound to give a methyl 5,6-diphenylpyridine-2-carboxylate derivative. These compounds can be reduced with diisobutylaluminum hydride to the corresponding aldehyde derivatives, which then can be converted into a number of homologs and derivatives. For instance, the aldehyde can be converted into a secondary amine by reacting it with a primary amine in the presence of a reducing agent, such as sodium cyanoborohydride. Alternatively, the aldehyde may be reduced to an alcohol and treated with an alkyl halide in the presence of a mild base to produce alkyl ethers. Those skilled in the art will recognize that these compounds may be used to prepare many other homologs, many of which are described in the Specific Examples section below.

DETAILED DESCRIPTION OF THE INVENTION

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like. Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

In the novel compounds of this invention $R^3$ and $R^4$ may be independently selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, preferably a carbocyclic aryl group having from 6 to 14 carbon atoms or a heterocyclic aryl group having from 2 to 14 carbon atoms and from 1 to 3 heteroatoms selected from the group consisting of nitrogen, oxygen and sulfur, halo, e.g. fluoro or chloro, $C_1$ to $C_{12}$ haloalkyl, e.g. trifluoromethyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, or sulfonyl groups.

$R^1$ and $R^2$ are aryl groups which may be any carbocyclic aryl or heterocyclic aryl group including but not limited to benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone. Such aryl groups can be bonded to the above moiety at any position. Such aryl group may itself be substituted with any common organic functional group including but not limited to alkyl, alkenyl, alkynyl, aryl, halo, haloalkyl, hydroxyl, alkoxyl, alkylcarbonyl, formyl, oxycarbonyl, carboxyl, alkyl carboxylate, alkyl amide, aminocarbonyl, amino, cyano, diazo, nitro, thio, sulfoxyl, or sulfonyl groups.

Preferably, the carbocyclic aryl group will comprise from 6 to 14 carbon atoms, e.g. from 6 to 10 carbon atoms. Preferably the heterocyclic aryl group will comprise from 2 to 14 carbon atoms and one or more, e.g. from 1 to 3 heteroatoms selected from the group consisting of nitrogen, oxygen and sulfur.

Preferably, R1 is selected from the groups consisting of phenyl and substituted derivatives thereof;

$R^2$ is selected, preferably from the group consisting of phenyl, furanyl, thienyl, pyridyl, pyranyl and substituted derivatives thereof;

$R^3$ is selected from the group consisting of H and lower alkyl;

$R^4$ is selected from the group consisting of H and lower alkyl; and a is 0 or an integer of from 1 to 3.

More preferably, $R^3$ is H.

In this more preferred embodiment of the invention, $R^1$ is represented, preferably, by the general formula

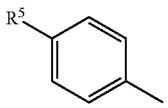

wherein R⁵ is selected from the group consisting of H, alkyl, trifluoromethyl, trifluoromethyloxy, halo, e.g. chloro, and loweralkylthio.

In said compounds, preferably, R² is selected from the group consisting of furanyl, thienyl, pyridyl and pyranyl or R² is represented by the general formula

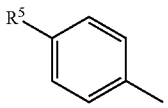

wherein R⁵ is selected from the group consisting of H, alkyl, trifluoromethyl, trifluoromethyloxy, halo, e.g. chloro, and loweralkylthio.

In one aspect of this invention X and Y are CR³ and Z is N.

In another aspect of this invention, the compounds have a side chain which is terminated with carboxylic acid or carboxylic ester group, i.e. b is 0, c is 1, x is 1, y is 1 and z is 0.

Preferably, in said carboxylic acid or ester terminated compounds a is 0 and more preferably R⁴ is alkyl.

In another aspect of the invention R¹ is a carbocyclic aryl having from 6 to 10 carbon atoms which may be substituted with an alkyl or halo alkyl group.

Preferably, R¹ is phenyl which may be substituted with an alkyl or haloalkyl group.

In still another aspect of the invention R² is a carbocyclic aryl having from 6 to 10 carbon atoms which may be substituted with an alkyl or haloalkyl group or R² is pyridyl.

Preferably said alkyl group is a lower alkyl radical and said haloalkyl group is trifluoromethyl.

In these phosphonic acid terminated compounds, preferably R³ is H, and

Furthermore, in said compounds, preferably c is 1, 2 or 3 and a is 1.

Finally, in said phosphonic acid-terminated compounds most preferably Z is N, X and Y are CR³, W is NR³, R² is phenyl and R⁵ is selected from the group consisting of H and methyl or R² is pyridyl and R⁵ is ethyl In another aspect of the present invention d is 0 and therefore the compounds have a side chain which terminates in a carbon-oxygen radical such as a carboxylic acid, an ester thereof, an ether, an alcohol, or an alkyl carboxy group.

In these carbon-oxygen terminated compounds, R¹ may be represented by the general formula

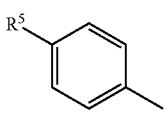

wherein R⁵ is selected from the group consisting of H, alkyl, trifluoromethyl, trifluoromethyloxy, halo, e.g. chloro, and loweralkylthio Furthermore R² may also be represented by the general formula

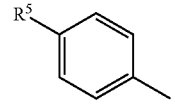

wherein R⁵ is selected from the group consisting of H, lower alkyl, trifluoromethyl, trifluoromethyloxy, halo, e.g. chloro, and loweralkylthio or R² is selected from the group consisting of furanyl, thienyl, pyridyl and pyranyl.

In such compounds, preferably R³ is H and more preferably, a is 1.

More preferably, in said compounds x is 1, z is 0 and R⁴ is selected from the group consisting of H, methyl and ethyl.

Finally, in the carbon-oxygen compounds of this invention preferably is Z is N, X and Y are CR³, R² is pyridyl, R⁴ is selected from the group consisting of methyl and ethyl and R⁵ is selected from the group consisting of H, methyl, ethyl, propyl and trifluoromethyl, or X, Y and Z are N, R⁴ is selected from the group consisting of methyl and ethyl and R⁵ is selected from the group consisting of H, methyl, ethyl, propyl and trifluoromethyl, or X and Z are N and Y is CR³.

Unless otherwise indicated, the following terms as used throughout this specification have the following meanings:

"Me" refers to methyl.
"Et" refers to ethyl.
"tBu" refers to t-butyl.
"iPr" refers to i-propyl.
"Ph" refers to phenyl.
"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, NO₂, halogen, dimethyl amino, and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, NO₂, halogen, dimethyl amino, and SH.

"Alkynyl" refers to a straight-chain, branched or cyclic unsaturated hydrocarbon containing at least one carbon-carbon triple bond. Preferably, the alkynyl group has 2 to 12 carbons. More preferably it is a lower alkynyl of from 2 to 7 carbons, most preferably 1 to 4 carbons. The alkynyl group may be optionally substituted with one or more substituents selected from the group consisting of hydroxyl, cyano, alkoxy, O, S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a—N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'''', where R'''' is aryl, C(CN)=C-aryl, $CH_2CN$, alkylaryl, sulfonamide, NH-alkyl, NH-alkylaryl, or NH-aryl.

SPECIFIC EXAMPLES

Specific compounds of the invention and their activity at the sphingosine-1-phosphate receptors are reported in Table I, below.

Compounds were also assessed for their ability to activate or block activation of the human S1P3 receptor in T24 cells stably expressing the human S1P3 receptor. Ten thousand cells/well were plated into 384-well poly-D-lysine coated plates one day prior to use. The growth media for the S1P3 receptor expressing cell line was McCoy's 5A medium supplemented with 10% charcoal-treated fetal bovine serum (FBS), 1% antibiotic-antimycotic and 400 µg/ml geneticin. On the day of the experiment, the cells were washed twice with Hank's Balanced Salt Solution supplemented with 20 mM HEPES (HBSS/Hepes buffer). The cells were then dye loaded with 2 uM Fluo-4 diluted in the HBSS/Hepes buffer with 1.25 mM Probenecid and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. The positive control, Sphingosine-1-Phosphate (S1P), was diluted in HBSS/Hepes buffer with 4 mg/ml fatty acid free bovine serum albumin. The FLIPR transferred 12.5 µl from the ligand microplate to the cell plate and took fluorescent measurements for 75 seconds, taking readings every second, and then for 2.5 minutes, taking readings every 10 seconds. Drugs were tested over the concentration range of 0.61 nM to 10,000 nM. Data for $Ca^{+2}$ responses were obtained in arbitrary fluorescence units and not translated into $Ca^{+2}$ concentrations. $IC_{50}$ values were determined through a linear regression analysis using the Levenburg Marquardt algorithm. In Table 1, NA is defined as "Not Active," ND is defined as "Not Determined," % efficacy is defined as "percent of receptor activity induced by a test compound at the highest dose test (10 µM) relative to the receptor activity induced by 5 nM sphingosine-1-phosphate," and % inhibition is defined as "percent of receptor activity induced by 5 nM sphingosine-1-phosphate that is inhibited by a test compound at the highest dose tested (10 µM)."

TABLE 1

| Example Number | Structure | S1P3 $EC_{50}$ (% efficacy) |
|---|---|---|
| 11 | 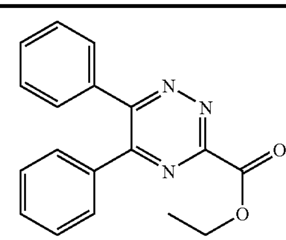 | NA |
| 12 | 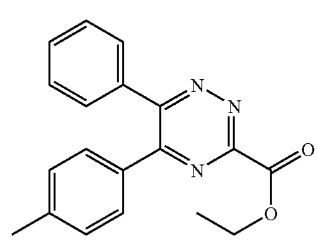 | NA |

TABLE 1-continued

| Example Number | Structure | S1P3 EC$_{50}$ (% efficacy) |
| --- | --- | --- |
| 13 | 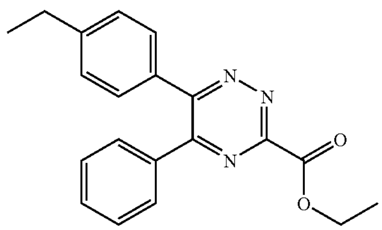 | 1.6 μM (0.57) |
| 14 | 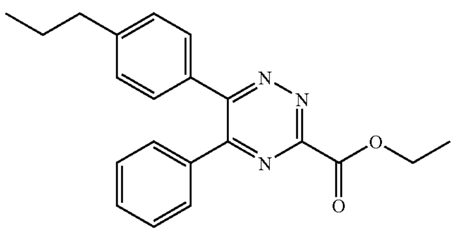 | NA |
| 15 | 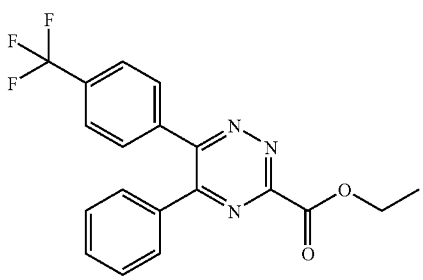 | NA |
| 16 | 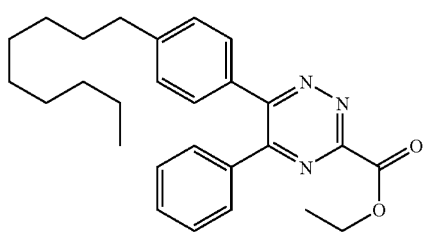 | NA |
| 17 | 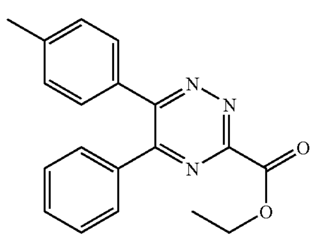 | 2.9 μM (ND) |
| 18 | 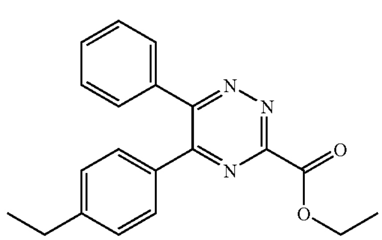 | NA |

TABLE 1-continued

| Example Number | Structure | S1P3 EC$_{50}$ (% efficacy) |
| --- | --- | --- |
| 19 | 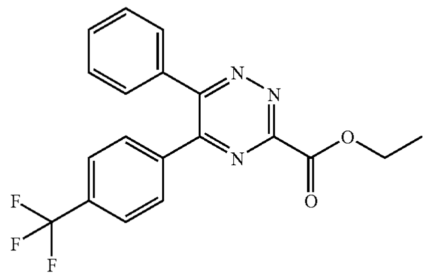 | 10 μM* (0.34) |
| 20 | 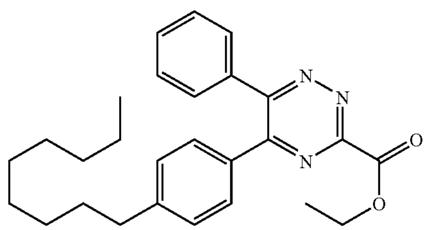 | NA |
| 21 | 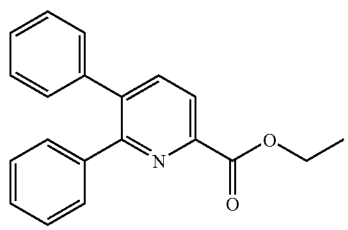 | 1.8 μM (0.80) |
| 22 | 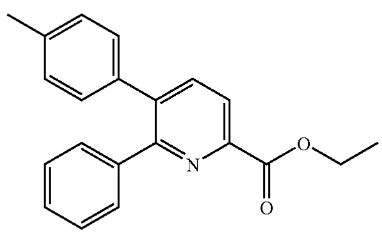 | 0.74 μM (0.32) |
| 23 | 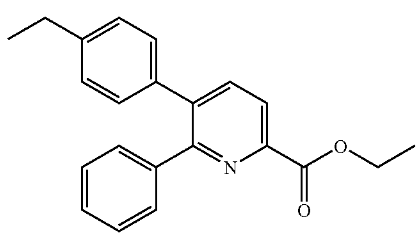 | 1.4 μM (0.82) |
| 24 | 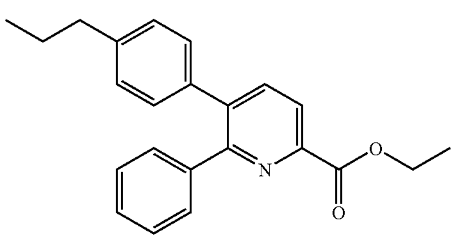 | 3.1 μM* (0.50) |

TABLE 1-continued
| Example Number | Structure | S1P3 EC$_{50}$ (% efficacy) |
|---|---|---|
| 27 | 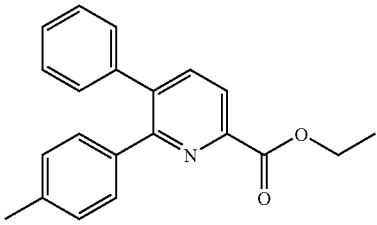 | 3.7 μM (0.46) |
| 28 | 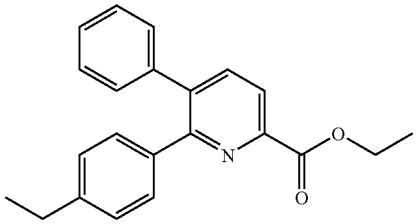 | 2.9 μM (0.48) |
| 30 | 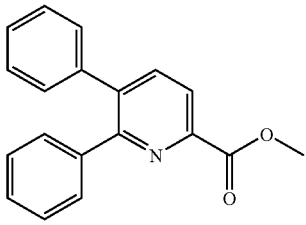 | 0.70 μM (0.84) |
| 31 | 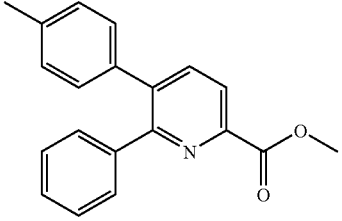 | 0.58 μM (0.73) |
| 32 | 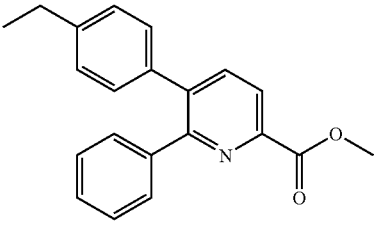 | 0.57 μM (0.88) |
| 33 | 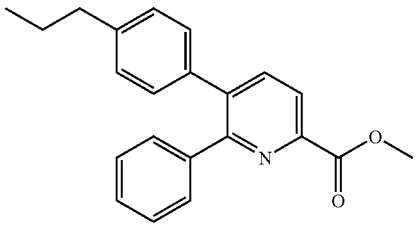 | 2.9 μM* (0.81) |

TABLE 1-continued

| Example Number | Structure | S1P3 EC$_{50}$ (% efficacy) |
|---|---|---|
| 34 | 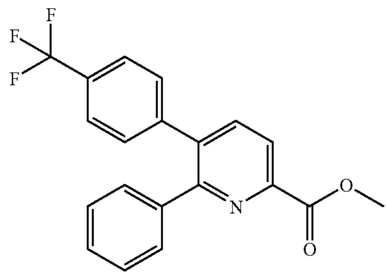 | NA |
| 35 | 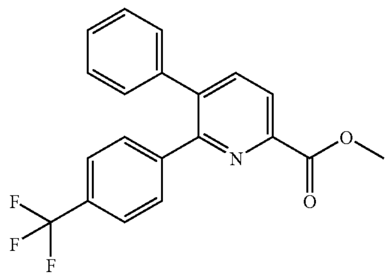 | 2.3 μM* (0.91) |
| 36 | 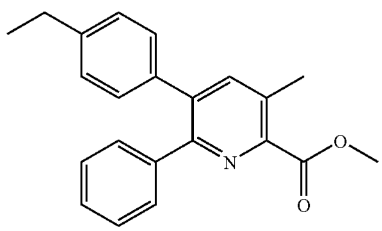 | NA |
| 51 | 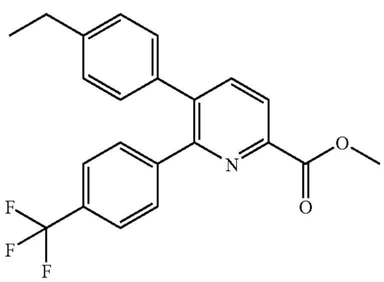 | NA |
| 52 | 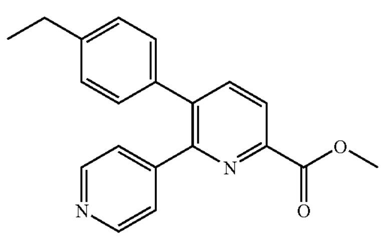 | 340 nM (0.90) |
| 53 | 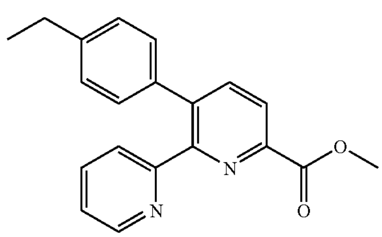 | NA |

TABLE 1-continued

| Example Number | Structure | S1P3 EC$_{50}$ (% efficacy) |
|---|---|---|
| 75 | 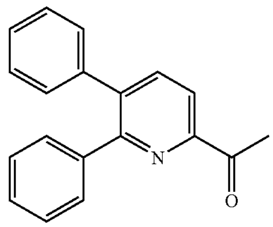 | >10 μM (0.51) |
| 76 | 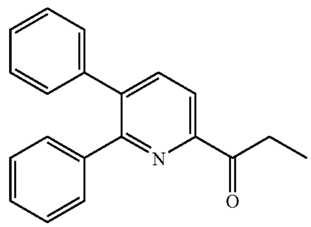 | 3.4 μM* (0.41) |
| 77 | 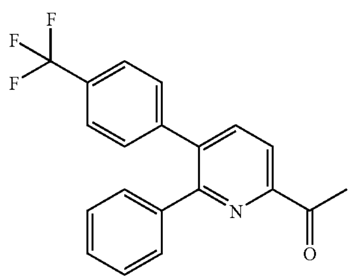 | NA |
| 78 | 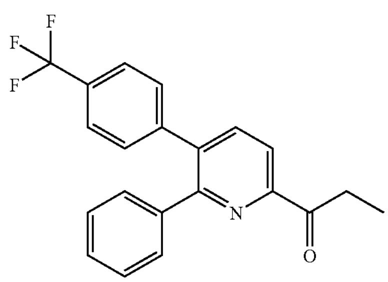 | NA |
| 79 | 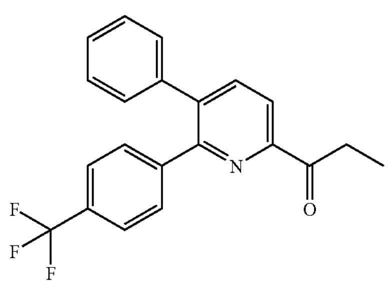 | 2.6 μM (0.30) |
| 80 | 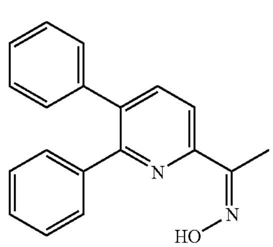 | NA |

TABLE 1-continued

| Example Number | Structure | S1P3 EC$_{50}$ (% efficacy) |
| --- | --- | --- |
| 81 | 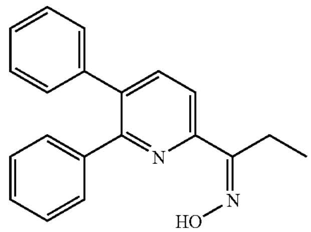 | NA |
| 82 | 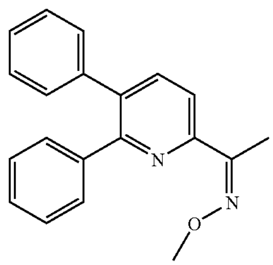 | NA |
| 83 | 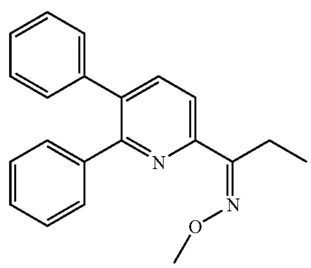 | NA |
| 84 | 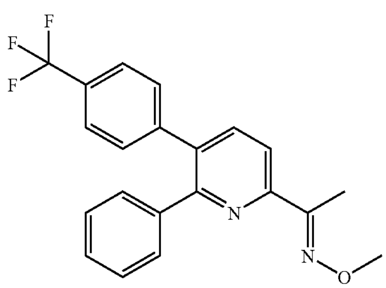 | NA |
| 85 | 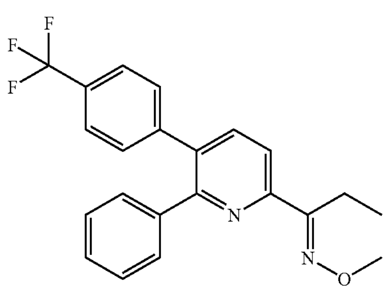 | NA |

TABLE 1-continued

| Example Number | Structure | S1P3 EC$_{50}$ (% efficacy) |
|---|---|---|
| 86 | 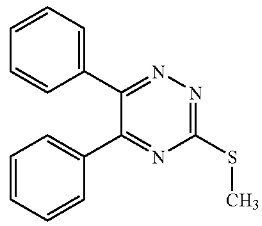 | NA |
| 87 | 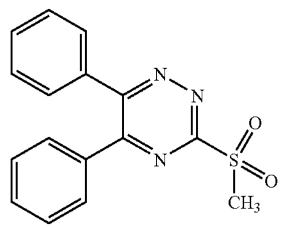 | NA |
| 88 | 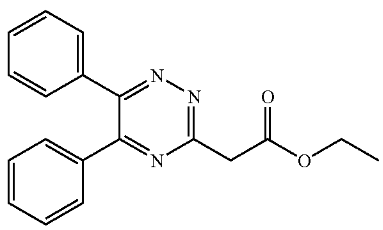 | NA |
| 89 | 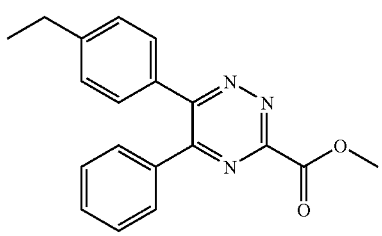 | 2.3 μM (0.64) |
| 90 | 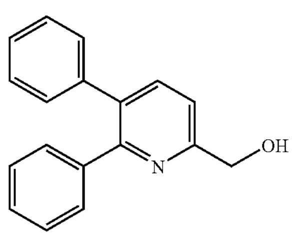 | NA |
| 91 | 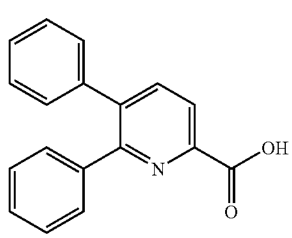 | NA |

TABLE 1-continued
| Example Number | Structure | S1P3 EC$_{50}$ (% efficacy) |
|---|---|---|
| 92 | 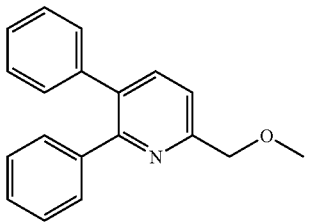 | 2.4 µM (0.59) |
| 93 | 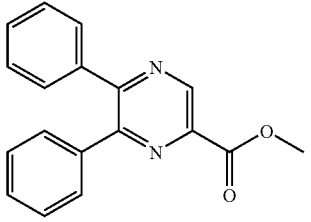 | 4.1 µM (0.62) |
| 94 | 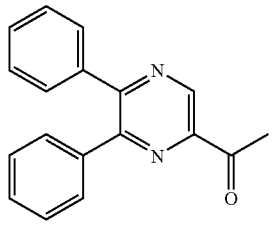 | 2.3 µM (0.61) |
| 95 | 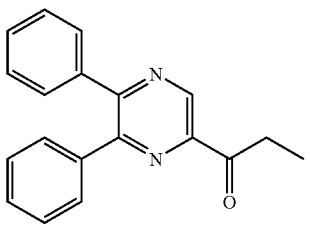 | 4.4 µM* (0.95) |
| 96 | 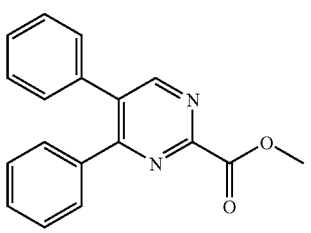 | NA |
| 97 | 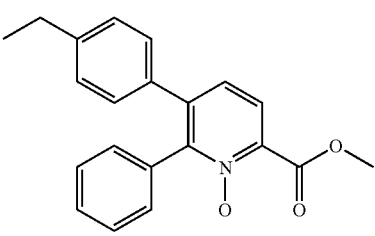 | NA |

TABLE 1-continued

| Example Number | Structure | S1P3 EC$_{50}$ (% efficacy) |
|---|---|---|
| 98 | 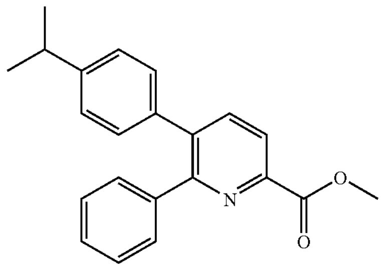 | ND |
| 99 | 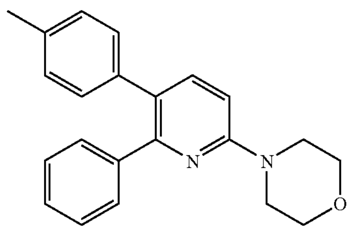 | NA |

As a result of the above activity of the compounds utilized in the method of the present invention, it is clear that such compounds may be used in treating the following diseases and conditions for the following reasons.

Pain
S1P increases capsaicin responsiveness of DRG neurons
S1P pathway, S1P3, S1P1 deregulated in multiple pain models
(EHT/AGN)
Glaucoma
S1P1/3 subtypes expressed in primary HTM cells
S1P decreases outflow facility >30% in perfused porcine eyes (See IOVS 45, 2263; 2004)
    Altered paracellular permeability
Dry Eye/Immunology
Induces lymphocyte sequestration without affecting T cell proliferation
Angiogenesis Disorders
siRNA knockdown of S1P1 and S1P3 inhibits angiogenesis
    S1P1/3 subtypes expressed in VEC
        promote VEC migration
        promote barrier assembly and integrity
Cardiovascular (S1P3)
S1P3 "knock out" mice lack S1P induced COPD
S1P3 agonism is dose limiting effect of FTY720
Wound Healing
S1P is released from activated platelets The invention is further illustrated by the following examples which are illustrative of a specific mode of practicing the invention and are not intended as limiting the scope of the claims.

The foregoing description details specific methods and compositions that can be employed to practice the present invention, and represents the best mode contemplated. Thus, however detailed the foregoing may appear in text, it should not be construed as limiting the overall scope hereof; rather, the ambit of the present invention is to be governed only by the lawful construction of the appended claims. Unless otherwise indicated, the following Chemical Abbreviations are used in the examples:

NH$_4$Cl: ammonium chloride
CHCl$_3$: chloroform
Et$_2$O: diethyl ether
DIBAL-H: diisobutylaluminum hydride
DME: 1,2-dimethoxyethane
DMF: N,N-dimethylformamide
DMSO: dimethylsulfoxide
EtOH: ethanol
EtOAc: ethyl acetate
HCl: hydrogen chloride or hydrochloric acid
NH$_2$OH—HCl: hydroxylamine hydrochloride
MeI: iodomethane
i-PrOH: isopropanol
MgSO$_4$: magnesium sulfate
MeOH: methanol
NH$_2$OMe—HCl: methoxylamine hydrochloride
CH$_2$Cl$_2$: methylene chloride
KOH: potassium hydroxide
K$_2$CO$_3$: potassium carbonate
PTLC: preparative thin layer chromatography
MPLC: medium pressure liquid chromatography
RuCl2(PPh3)4: Na: sodium
NaOEt: sodium ethoxide
NaOH: sodium hydroxide
Na$_2$SO$_4$: sodium sulfate NaHCO$_3$: sodium bicarbonate
NaBH$_4$: sodium borohydride
NaBH$_3$CN: sodium cyanoborohydride
NaH: sodium hydride
H$_2$SO$_4$: sulfuric acid
Bu$_4$NOH: tetrabutylammonium hydroxide
THF: tetrahydrofuran
Pd(PPh$_3$)$_4$: palladium tetrakis(triphenylphosphine)
TMSI: iodotrimethylsilane All other chemicals were purchased from Aldrich Chemical Company, and they were used as provided.

Example 1

1-(2-p-Tolylethynyl)benzene (Compound 1). General Procedure A. To a solution of lithium phenylacetylide (15.2 ml, 15.2 mmol) in DME (20 ml) under Argon at −78° C. was added triisopropoxylborane (3.5 ml, 15.2 mmol). The mixture was stirred at −78° C. for 1.5 hours. A solution of 1-bromo-4-methylbenzene (2 g, 11.7 mmol) in DME/THF (10 ml/10 ml) was degassed with dry argon, Pd(PPh$_3$)$_4$ (405 mg, 0.35 mmol) was added and the solution was degassed for another 5 min.

The degassed solution was cannulated into the first solution, and the mixture was heated under argon at 85° C. for 2 hours. The mixture was cooled to room temperature, and it was diluted with ethyl acetate, and washed with water. The

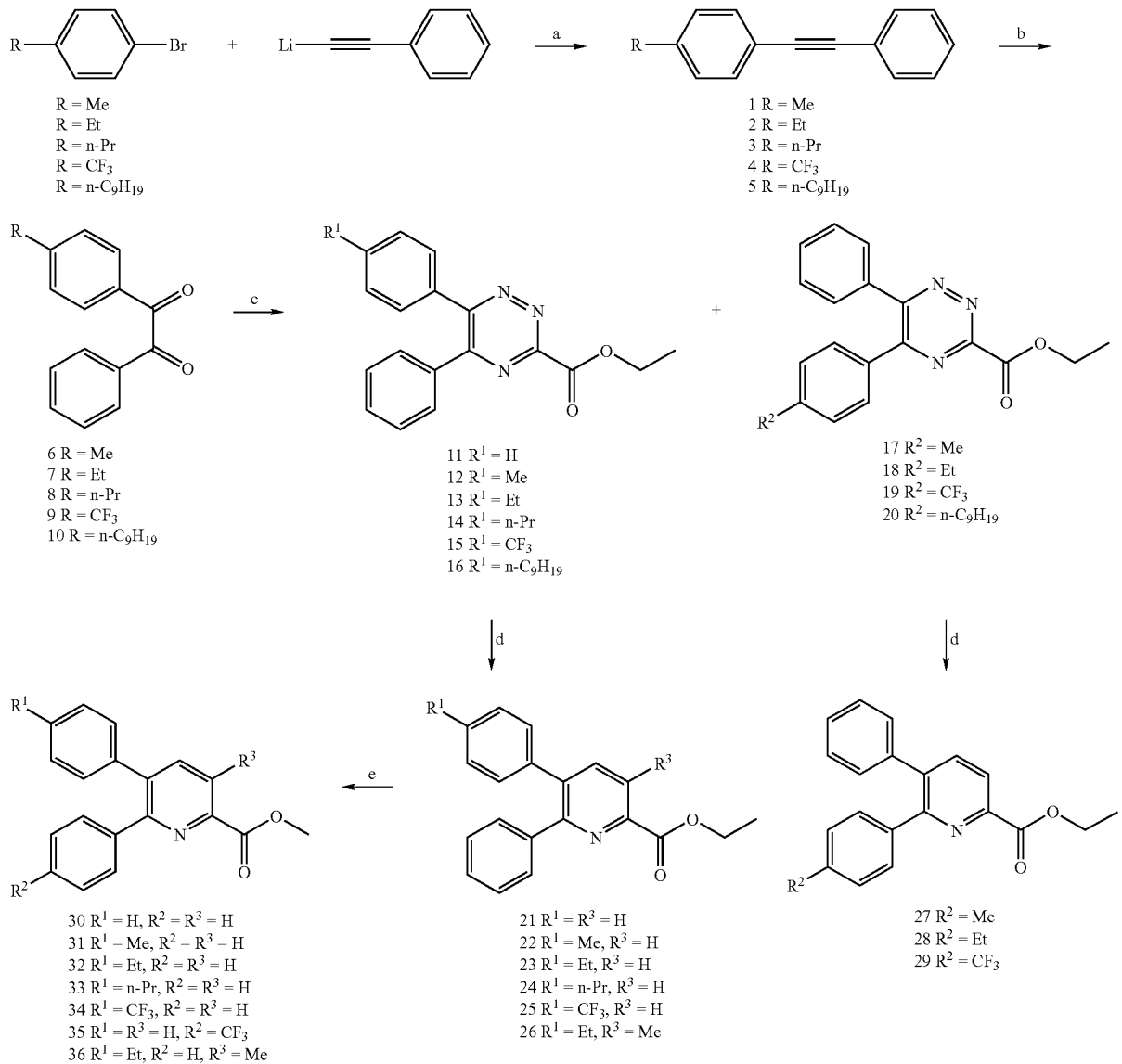

Scheme 1

(a) B(OiPr)$_3$, Pd(PPh$_3$)$_4$, DME, THF, 90° C., 2 hours; (b) RuCl$_2$(PPh$_3$)$_3$, PhIO, CH$_2$Cl$_2$; (c) ethyl oxalamidrazonate, ethanol; (d) i) pyrrolidine, CH$_3$CHO, K$_2$CO$_3$, toluene, ii) CHCl$_3$, 72° C.; (e)c. H$_2$SO$_4$, MeOH, 70° C.

separated organic layer was washed with water and brine, and dried over $MgSO_4$. The filtered solvent was concentrated in vacuo, and the residue was purified by column chromatography (silica, 5% ethyl acetate in hexane) to give the title compound as a yellow solid.

$^1$H NMR (300 MHz, $CDCl_3$): δ 2.37 (s, 3H), 7.16 (d, J=8.50 Hz, 2H), 7.29-7.38 (m, 3H), 7.43 (d, J=7.92 Hz, 2H), 7.48-7.56 (m, 2H).

Example 2

1-(2-(4-Ethylphenyl)ethynyl)benzene (Compound 2) Following General Procedure A, lithium phenylacetylide (14.0 ml, 14.1 mmol), triisopropoxylborane (3.2 ml, 14.1 mmol), 1-bromo-4-ethylbenzene (2 g, 10.8 mmol) and $Pd(PPh_3)_4$ (375 mg, 0.32 mmol) in DME (30 ml) and THF (10 ml) were reacted to obtain the title compound as a yellow oil.

$^1$H NMR (300 MHz, $CDCl_3$): δ 1.24 (t, J=7.62 Hz, 3H), 2.66 (q, J=7.62 Hz, 2H), 7.18 (d, J=8.21 Hz, 2H), 7.28-7.39 (m, 3H), 7.45 (d, J=8.21 Hz, 2H), 7.49-7.56 (m, 2H).

Example 3

1-(2-(4-n-Propylphenyl)ethynyl)benzene (Compound 3) Following General Procedure A, lithium phenylacetylide (13.0 ml, 13.1 mmol), triisopropoxylborane (3.0 ml, 13.1 mmol), 1-bromo-4-n-propylbenzene (2 g, 10.1 mmol) and $Pd(PPh_3)_4$ (348 mg, 0.30 mmol) in DME (30 ml) and THF (10 ml) were reacted to obtain the title compound as a yellow oil.

$^1$H NMR (300 MHz, $CDCl_3$) δ 0.94 (t, J=7.33 Hz, 17H), 1.57-1.73 (m, 2H), 2.57-2.62 (m, 2H), 7.16 (d, J=8.50 Hz, 2H), 7.29-7.40 (m, J=2.05 Hz, 3H), 7.44 (d, J=8.50 Hz, 2H), 7.49-7.55 (m, 2H).

Example 4

1-(2-(4-Trifluoromethylphenyl)ethynyl)benzene (Compound 4) Following General Procedure A, lithium phenylacetylide (17.3 ml, 17.3 mmol), triisopropoxylborane (4.0 ml, 17.3 mmol), 1-bromo-4-trifluoromethyl-benzene (3 g, 13.3 mmol) and $Pd(PPh_3)_4$ (462 mg, 0.40 mmol) in DME (40 ml) and THF (15 ml) were reacted to obtain the title compound as a yellow solid.

$^1$H NMR (300 MHz, $CDCl_3$) δ 7.31-7.42 (m, 3H), 7.50-7.58 (m, 2H), 7.57-7.68 (m, 4H).

Example 5

1-(2-(4-n-Nonanylphenyl)ethynyl)benzene (Compound 5) Following General Procedure A, lithium phenylacetylide (12.4 ml, 12.4 mmol), triisopropoxylborane (2.8 ml, 12.4 mmol), 1-bromo-4-n-nonanylbenzene (2.7 g, 9.5 mmol) and $Pd(PPh_3)_4$ (331 mg, 0.40 mmol) in DME (30 ml) and THF (10 ml) were reacted to obtain the title compound as a yellow solid.

$^1$H NMR (300 MHz, $CDCl_3$) δ 0.88 (t, J=7.04 Hz, 3H), 1.17-1.38 (m, 12H), 1.54-1.68 (m, 2H), 2.55-2.65 (m, 2H), 7.15 (d, J=8.21 Hz, 2H), 7.28-7.39 (m, 3H), 7.44 (d, J=8.21 Hz, 2H), 7.48-7.56 (m, 2H).

Example 6

1-Phenyl-2-p-tolylethane-1,2-dione (Compound 6). General Procedure B. To a suspension of iodosobenzene (2.5 g, 11.3 mmol) in $CH_2Cl_2$ (30 ml) was added $RuCl_2(PPh_3)_4$ (45 mg, 0.04 mmol). A solution of 1-(2-p-tolylethynyl)benzene (Compound 1, 835 mg, 4.3 mmol) in $CH_2Cl_2$ (10 ml) was cannulated into the suspension. The resulting mixture was stirred at room temperature overnight resulting in a homogeneous solution. The solvent was removed in vacuo, and the residue was purified by silica gel chromatography (10% ethyl acetate in hexane) to produce the title compound as a yellow oil.

$^1$H NMR (300 MHz, $CDCl_3$) δ 2.44 (s, 3H), 7.31 (d, J=7.92 Hz, 2H), 7.51 (t, J=7.62 Hz, 2H), 7.59-7.71 (m, 1H), 7.87 (d, J=8.21 Hz, 2H), 7.92-8.00 (m, 2H).

Example 7

1-(4-Ethyl-phenyl)-2-phenyl-ethane-1,2-dione (Compound 7). Following General Procedure B, iodosobenzene (1.5 g, 6.7 mmol), $RuCl_2(PPh_3)_4$ (21 mg, 0.02 mmol) and 1-(2-(4-ethylphenyl)ethynyl)benzene (Compound 2, 360 mg, 1.8 mmol) in $CH_2Cl_2$ (30 ml) were reacted to produce the title compound as a yellow oil.

$^1$H NMR (300 MHz, $CDCl_3$) δ 1.26 (t, J=7.62 Hz, 3H), 2.73 (q, J=7.62 Hz, 2H), 7.34 (d, J=8.50 Hz, 2H), 7.45-7.56 (m, 2H), 7.59-7.70 (m, 1H), 7.90 (d, J=8.21 Hz, 2H), 7.93-8.01 (m, 2H).

Example 8

1-(4-n-Propyl-phenyl)-2-phenyl-ethane-1,2-dione (Compound 8). Following General Procedure B, iodosobenzene (2.2 g, 10.0 mmol), $RuCl_2(PPh_3)_4$ (38 mg, 0.04 mmol) and 1-(2-(4-n-propylphenyl)ethynyl)benzene (Compound 3, 860 mg, 3.9 mmol) in $CH_2Cl_2$ (50 ml) were reacted to produce the title compound as a yellow oil.

$^1$H NMR (300 MHz, $CDCl_3$) δ 0.95 (t, J=7.62 Hz, 3H), 1.58-1.76 (m, 2H), 2.60-2.69 (m, 2H), 7.31 (d, J=8.21 Hz, 2H), 7.46-7.56 (m, 2H), 7.61-7.70 (m, 1H), 7.89 (d, J=8.21 Hz, 2H), 7.94-8.01 (m, 2H).

Example 9

1-(4-Trifluoromethyl-phenyl)-2-phenyl-ethane-1,2-dione (Compound 9). Following General Procedure B, iodosobenzene (5.5 g, 24.3 mmol), $RuCl_2(PPh_3)_4$ (96 mg, 0.10 mmol) and 1-(2-(4-trifluoromethyl phenyl)ethynyl)benzene (Compound 4, 1.9 g, 8.1 mmol) in $CH_2Cl_2$ (100 ml) were reacted to produce the title compound as a yellow solid.

$^1$H NMR (300 MHz, $CDCl_3$) δ 7.49-7.59 (m, 2H), 7.65-7.74 (m, 1H), 7.79 (d, J=8.21 Hz, 2H), 7.94-8.02 (m, 2H), 8.11 (d, J=8.21 Hz, 2H).

Example 10

1-(4-n-Nonanylphenyl)-2-phenylethane-1,2-dione (Compound 10). Following General Procedure B, iodosobenzene (744 mg, 3.39 mmol), $RuCl_2(PPh_3)_4$ (11 mg, 0.01 mmol) and 1-(2-(4-n-nonanylphenyl)ethynyl)benzene (Compound 5, 343 mg, 1.12 mmol) in $CH_2Cl_2$ (30 ml) were reacted to produce the title compound as a yellow oil.

$^1$H NMR (300 MHz, $CDCl_3$) δ 0.87 (t, J=6.74 Hz, 3H), 1.14-1.40 (m, 12H), 1.55-1.71 (m, 2H), 7.48-7.53 (m, 2H), 7.60-7.72 (m, 1H), 7.88 (d, J=8.21 Hz, 2H), 7.94-8.02 (m, 2H).

Example 11

Ethyl 5,6-Diphenyl-1,2,4-triazine-3-carboxylate (Compound 11). General Procedure C. A solution of ethyl oxalamidrazonate (Compound 37, 236 mg, 1.8 mmol) in ethanol (20 ml) was cannulated slowly into a stirring solution of benzil (500 mg, 2.4 mmol) in ethanol (20 ml) under argon at room temperature. After the addition was completed, the reaction was stirred at room temperature overnight (~16 hours). The mixture was then refluxed for 1 hour. The solvent was removed in vacuo, and the crude products was purified by column chromatography (silica gel, 20% ethyl acetate in hexane) to obtain the title compound as an oil.

$^1$H NMR (300 MHz, acetone-d$_6$) δ 1.45 (t, J=7.04 Hz, 3H), 4.54 (q, J=7.13 Hz, 2H), 7.38-7.58 (m, 6H), 7.61-7.72 (m, 4H).

Example 12 and Example 17

Ethyl 6-Phenyl-5-p-tolyl-1,2,4-triazine-3-carboxylate (Compound 12), and Ethyl 5-Phenyl-6-p-tolyl-1,2,4-triazine-3-carboxylate (Compound 17). Following General Procedure C, ethyl oxalamidrazonate (Compound 37, 121 mg, 0.9 mmol), 1-phenyl-2-p-tolylethane-1,2-dione (Compound 6, 268 mg, 1.2 mmol) in ethanol (10 ml) were reacted, and the products were separated by recrystallization from 5% ethyl acetate in hexane to produce Compound 12 and Compound 17 as yellow solids.

Compound 12: $^1$H NMR (300 MHz, CDCl$_3$): δ 1.50 (t, J=7.33 Hz, 3H), 2.39 (s, 3H), 4.61 (q, J=7.04 Hz, 2H), 7.19 (d, J=7.92 Hz, 2H), 7.32-7.49 (m, 3H), 7.52 (d, J=8.21 Hz, 2H), 7.63-7.69 (m, 2H).

Compound 17: $^1$H NMR (300 MHz, CDCl$_3$): δ 1.51 (t, J=7.04 Hz, 3H), 2.37 (s, 3H), 4.61 (q, J=7.04 Hz, 2H), 7.15 (d, J=7.92 Hz, 2H), 7.35-7.51 (m, 3H), 7.56 (d, J=8.50 Hz, 2H), 7.60-7.66 (m, 2H).

Example 13 and Example 18

Ethyl 6-(4-Ethylphenyl)-5-phenyl-1,2,4-triazine-3-carboxylate (Compound 13), and Ethyl 5-(4-Ethylphenyl)-6-phenyl-1,2,4-triazine-3-carboxylate (Compound 18). Following General Procedure C, ethyl oxalamidrazonate (Compound 37, 117 mg, 0.9 mmol) and 1-(4-Ethyl-phenyl)-2-phenyl-ethane-1,2-dione (Compound 7, 276 mg, 1.2 mmol) in ethanol (10 ml) were reacted, and the products were separated by recrystallization from 5% ethyl acetate in hexane to produce Compound 13 and Compound 18 as yellow solids.

Compound 13: $^1$H NMR (300 MHz, CDCl$_3$): δ 1.26 (t, J=7.81 Hz, 3H), 1.51 (t, J=7.32 Hz, 3H), 2.69 (q, J=7.81 Hz, 2H), 4.61 (q, J=7.32 Hz, 2H), 7.23 (d, J=7.32 Hz, 2H), 7.35-7.38 (m, 2H), 7.45-7.47 (m, 1H), 7.56 (d, J=8.30 Hz, 2H), 7.67 (d, J=7.81 Hz, 2H).

Compound 18: $^1$H NMR (300 MHz, CDCl$_3$): δ 1.23 (t, J=7.81 Hz, 3H), 1.51 (t, J=7.32 Hz, 3H), 2.67 (q, J=7.81 Hz, 2H), 4.62 (q, J=7.32 Hz, 2H), 7.19 (d, J=8.79 Hz, 2H), 7.39-7.42 (m, 2H), 7.45-7.48 (m, 1H), 7.59 (d, J=8.30 Hz, 2H), 7.65 (d, J=8.30 Hz, 2H).

Example 14

Ethyl 5-Phenyl-6-(4-propylphenyl)-1,2,4-triazine-3-carboxylate (Compound 14). Following General Procedure C, ethyl oxalamidrazonate (Compound 37, 460 mg, 1.5 mmol) and 1-(4-n-propylphenyl)-2-phenyl-ethane-1,2-dione (Compound 8, 588 mg, 2.3 mmol) in ethanol (40 ml) were reacted and the product was recrystallized from 5% ethyl acetate in hexane to produce the title compound as yellow solid.

$^1$H NMR (300 MHz, CDCl$_3$) δ 0.95 (t, J=7.33 Hz, 3H), 1.51 (t, J=7.04 Hz, 3H), 1.62-1.74 (m, 2H), 2.55-2.63 (m, 2H), 4.61 (q, J=7.13 Hz, 2H), 7.20 (d, J=8.50 Hz, 2H), 7.32-7.49 (m, 3H), 7.50-7.57 (m, 2H), 7.62-7.70 (m, 2H).

Example 15 and Example 19

Ethyl 6-(4-Trifluoromethyl-phenyl)-5-phenyl-1,2,4-triazine-3-carboxylate (Compound 15), and Ethyl 5-(4-Trifluoromethylphenyl)-6-phenyl-1,2,4-triazine-3-carboxylatate (Compound 19). Following General Procedure C, ethyl oxalamidrazonate (Compound 37, 1.2 g, 8.8 mmol) and 1-(4-trifluoromethylphenyl)-2-phenyl-ethane-1,2-dione (Compound 9, 1.6 g, 5.9 mmol) in ethanol (40 ml) were reacted, and the products were separated by recrystallization from 5% ethyl acetate in hexane to produce Compound 15 and Compound 19 as yellow solids.

Compound 15: $^1$H NMR (300 MHz, CDCl$_3$) δ 1.52 (t, J=7.18 Hz, 3H), 4.63 (q, J=7.04 Hz, 2H), 7.38-7.54 (m, 3H), 7.56-7.68 (m, 4H), 7.78 (d, J=8.21 Hz, 2H).

Compound 19: $^1$H NMR (300 MHz, CDCl$_3$) δ 1.52 (t, J=7.18 Hz, 3H), 4.63 (q, J=7.13 Hz, 2H), 7.35-7.54 (m, 3H), 7.59-7.70 (m, 4H), 7.73-7.81 (m, 2H).

Example 16 and Example 20

Ethyl 6-(4-Nonylphenyl)-5-phenyl-1,2,4-triazine-3-carboxylate (Compound 16), and Ethyl 5-(4-Nonylphenyl)-6-phenyl-1,2,4-triazine-3-carboxylate (Compound 20). Following General Procedure C, ethyl oxalamidrazonate (Compound 37, 108 mg, 0.83 mmol) and 1-(4-nonylphenyl)-2-phenylethane-1,2-dione (Compound 10, 252 mg, 0.75 mmol) in ethanol (10 ml) were reacted and the mixture purified by MPLC to isolate Compound 16 and Compound 20 as yellow oils.

Compound 16: $^1$H NMR (300 MHz, CDCl$_3$): δ 0.88 (t, J=7.04 Hz, 3H), 1.18-1.39 (m, 12H), 1.51 (t, J=7.18 Hz, 3H), 1.56-1.72 (m, 2H), 2.58-2.70 (m, 2H), 4.61 (q, J=7.23 Hz, 2H), 7.20 (d, J=8.21 Hz, 2H), 7.31-7.41 (m, 2H), 7.33-7.40 (m, 1H), 7.53 (d, J=8.21 Hz, 2H), 7.61-7.70 (m, 2H).

Compound 20: $^1$H NMR (300 MHz, CDCl$_3$): $^1$H NMR (300 MHz, Solvent) δ 0.88 (t, J=7.04 Hz, 3H), 1.17-1.37 (m, 12H), 1.52 (t, J=7.04 Hz, 3H), 1.55-1.66 (m, 2H), 2.54-2.69 (m, 2H), 4.62 (q, J=7.04 Hz, 2H), 7.16 (d, J=8.21 Hz, 2H), 7.33-7.53 (m, 3H), 7.58 (d, J=8.21 Hz, 2H), 7.60-7.70 (m, 2H).

Example 21

Ethyl 5,6-diphenylpyridine-2-carboxylate (Compound 21). General Procedure D. Ethyl 5,6-diphenyl-1,2,4-triazine-3-carboxylate (Compound 11, 200 mg, 0.66 mmol) and crude 1-vinylpyrrolidine (Compound 38, 2 g) in CHCl$_3$ (20 ml) was heated at 75° C. overnight under nitrogen. The solvent was removed in vacuo, and the residue was purified by silica gel column chromatography (20% ethyl acetate in hexane) to yield the title compound as a light yellow solid.

$^1$H NMR (300 MHz, CDCl$_3$) δ 1.46 (t, J=7.18 Hz, 3H), 4.50 (q, J=7.13 Hz, 2H), 7.13-7.33 (m, 8H), 7.35-7.44 (m, 2H), 7.84 (d, J=7.92 Hz, 1H), 8.12 (d, J=7.92 Hz, 1H).

Example 22

Ethyl 6-Phenyl-5-p-tolyl-pyridine-2-carboxylate (Compound 22). Following General Procedure D, ethyl 5-phenyl-6-p-tolyl-1,2,4-triazine-3-carboxylate (Compound 12, 177 mg, 0.56 mmol) and crude 1-vinylpyrrolidine (Compound 38, 730 mg) in CHCl$_3$ (10 ml) were reacted to produce the title compound as a yellow solid.

$^1$H NMR (300 MHz, CDCl$_3$) δ 1.45 (t, J=7.18 Hz, 3H), 2.34 (s, 3H), 4.49 (q, J=7.04 Hz, 2H), 7.05-7.11 (m, 4H), 7.17-7.28 (m, 3H), 7.36-7.44 (m, 2H), 7.82 (d, J=7.92 Hz, 1H), 8.10 (d, J=7.92 Hz, 1H).

Example 23

Ethyl 5-(4-Ethyl-phenyl)-6-phenyl-pyridine-2-carboxylate (Compound 23). Following General Procedure D, ethyl 6-(4-ethyl-phenyl)-5-phenyl-1,2,4-triazine-3-carboxylate (Compound 13, 105 mg, 0.30 mmol) and crude 1-vinylpyrrolidine (Compound 38, 2 g) in $CHCl_3$ (10 ml) were reacted to produce the title compound as a yellow solid.

$^1$H NMR (300 MHz, $CDCl_3$) δ 1.19 (t, J=7.62 Hz, 3H), 1.45 (t, J=7.04 Hz, 3H), 2.58 (q, J=7.62 Hz, 2H), 4.47 (q, J=7.04 Hz, 2H), 7.09-7.16 (m, 4H), 7.22-7.30 (m, 3H), 7.36-7.42 (m, 2H), 7.83 (d, J=7.92 Hz, 1H), 8.10 (d, J=7.91 Hz, 1H).

Example 24

Ethyl 6-Phenyl-5-(4-propylphenyl)-pyridine-2-carboxylate (Compound 24). Following General Procedure D, ethyl 5-phenyl-6-(4-propyl-phenyl)-1,2,4-triazine-3-carboxylate (Compound 14), (153 mg, 0.46 mmol) and crude 1-vinylpyrrolidine (Compound 38, 2 g) in $CHCl_3$ (10 ml) were reacted to produce the title compound as a yellow oil.

$^1$H NMR (300 MHz, $CDCl_3$) δ 0.94 (t, J=7.33 Hz, 3H), 1.45 (t, J=7.04 Hz, 3H), 1.56-1.72 (m, 2H), 2.55-2.62 (m, 2H), 4.49 (q, J=7.23 Hz, 2H), 7.09 (s, 4H), 7.20-7.30 (m, 3H), 7.36-7.45 (m, 2H), 7.84 (d, J=7.92 Hz, 1H), 8.11 (d, J=7.92 Hz, 1H).

Example 25

Ethyl 6-Phenyl-5-(4-trifluoromethylphenyl)-pyridine-2-carboxylate (Compound 25). Following General Procedure D, ethyl 6-(4-trifluoromethylphenyl)-5-phenyl-1,2,4-triazine-3-carboxylate (Compound 15), (378 mg, 1.01 mmol) and crude 1-vinylpyrrolidine (Compound 38, 780 mg) in $CHCl_3$ (10 ml) were reacted to produce the title compound as a yellow oil.

$^1$H NMR (300 MHz, $CDCl_3$) δ 1.47 (t, J=7.18 Hz, 3H), 4.52 (q, J=7.04 Hz, 2H), 7.15-7.22 (m, 2H), 7.30-7.36 (m, 3H), 7.47-7.58 (m, 4H), 8.18 (d, J=7.92 Hz, 1H).

Example 26

Ethyl 5-(4-Ethylphenyl)-3-methyl-6-phenyl-pyridine-2-carboxylate (Compound 26). Following General Procedure D, ethyl 6-(4-ethylphenyl)-5-phenyl-1,2,4-triazine-3-carboxylate (Compound 13, 200 mg, 0.60 mmol) and crude 1-propenyl-pyrrolidine (Compound 39, 2 g) in $CHCl_3$ (10 ml) were reacted to produce the title compound as a yellow oil.

$^1$H NMR (500 MHz, $CDCl_3$) δ 1.23 (t, J=7.81 Hz, 3H), 1.45 (t, J=7.08 Hz, 3H), 2.56-2.69 (m, 5H), 4.47 (q, J=7.08 Hz, 2H), 7.01-7.15 (m, 4H), 7.16-7.30 (m, 3H), 7.35-7.42 (m, 2H), 7.60 (s, 1H).

Example 27

Ethyl 5-Phenyl-6-p-tolyl-pyridine-2-carboxylate (Compound 27). Following General Procedure D, ethyl 6-phenyl-5-p-tolyl-1,2,4-triazine-3-carboxylate (Compound 17, 361 mg, 1.13 mmol) and crude 1-vinylpyrrolidine (Compound 38, 806 mg) in $CHCl_3$ (10 ml) were reacted to produce the title compound as a yellow oil.

$^1$H NMR (300 MHz, $CDCl_3$) δ 1.45 (t, J=7.18 Hz, 3H), 2.30 (s, 3H), 4.49 (q, J=7.04 Hz, 2H), 7.05 (d J=7.92 Hz, 2H), 7.14-7.24 (m, 2H), 7.27-7.33 (m, 5H), 7.82 (d, J=7.92 Hz, 1H), 8.09 (d, J=7.91 Hz, 1H).

Example 28

Ethyl 6-(4-Ethylphenyl)-5-phenyl-pyridine-2-carboxylate (Compound 28). Following General Procedure D, ethyl 5-(4-ethylphenyl)-6-phenyl-1,2,4-triazine-3-carboxylate (Compound 18, 245 mg, 0.74 mmol) and crude 1-vinylpyrrolidine (Compound 38, 572 mg) in $CHCl_3$ (10 ml) were reacted to produce the title compound as a yellow oil.

$^1$H NMR (300 MHz, $CDCl_3$) δ 1.19 (t, J=7.62 Hz, 3H), 1.45 (t, J=7.18 Hz, 3H), 2.60 (q, J=7.62 Hz, 2H), 4.49 (q, J=7.04 Hz, 2H), 7.06 (d, J=7.92 Hz, 2H), 7.27-7.36 (m, 5H), 7.82 (d, J=7.92 Hz, 1H), 8.09 (d, J=7.91 Hz, 1H).

Example 29

Ethyl 5-Phenyl-6-(4-trifluoromethyl-phenyl)-pyridine-2-carboxylate (Compound 29). Following General Procedure D, ethyl 5-(4-trifluoromethylphenyl)-6-phenyl-1,2,4-triazine-3-carboxylate (Compound 19, 1 g, 2.68 mmol) and crude 1-vinylpyrrolidine (Compound 38, 1.4 g) in $CHCl_3$ (20 ml) were reacted to produce the title compound as a yellow oil.

$^1$H NMR (300 MHz, $CDCl_3$) δ 1.46 (t, J=7.18 Hz, 12H), 4.51 (q, J=7.23 Hz, 2H), 7.21-7.42 (m, 5H), 7.85 (d, J=7.92 Hz, 1H), 8.15 (d, J=8.21 Hz, 1H).

Example 30

Methyl 5,6-diphenylpyridine-2-carboxylate (Compound 30). General Procedure E. A solution of ethyl 5,6-diphenylpyridine-2-carboxylate (Compound 21, 30 mg, 0.1 mmol) and conc. $H_2SO_4$ (3 drops) in MeOH (5 ml) was heated at 50° C. overnight. The mixture was diluted with water, and the products were extracted with ethyl acetate. The organic layer was washed with water and brine, and dried over $Na_2SO_4$. The filtered solvent was concentrated in vacuo and the residue was purified by column chromatography (20% ethyl acetate in hexane) to obtain the title compound as a yellow solid.

$^1$H NMR (500 MHz, $CDCl_3$) δ 4.02 (s, 3H), 7.15-7.31 (m, 8H), 7.38 (d, J=7.81 Hz, 2H), 7.86 (d, J=8.30 Hz, 1H), 8.15 (d, J=7.81 Hz, 1H).

Example 31

Methyl 6-Phenyl-5-p-tolyl-pyridine-2-carboxylate (Compound 31). Following General Procedure E, ethyl 6-phenyl-5-p-tolyl-pyridine-2-carboxylate (Compound 22, 70 mg, 0.22 mmol) and conc. $H_2SO_4$ (3 drops) in MeOH (3 ml) were reacted to produce the title compound as a yellow solid.

$^1$H NMR (300 MHz, $CDCl_3$) δ 2.34 (s, 3H), 4.01 (s, 3H), 7.05-7.11 (m, 4H), 7.19-7.30 (m, 3H), 7.35-7.44 (m, 2H), 7.84 (d, J=7.92 Hz, 1H), 8.13 (d, J=7.92 Hz, 1H).

Example 32

Methyl 5-(4-Ethylphenyl)-6-phenyl-pyridine-2-carboxylate (Compound 32). Following General Procedure E, ethyl 5-(4-ethylphenyl)-6-phenylpyridine-2-carboxylate (Compound 23, 45 mg, 0.15 mmol) and conc. $H_2SO_4$ (3 drops) in MeOH (3 ml) were reacted to produce title compound as a yellow solid.

$^1$H NMR (300 MHz, $CDCl_3$) δ 1.23 (t, J=7.62 Hz, 3H), 2.64 (q, J=7.62 Hz, 2H), 4.02 (s, 3H), 7.05-7.16 (m, 4H), 7.19-7.29 (m, 3H), 7.34-7.44 (m, 2H), 7.84 (d, J=7.92 Hz, 1H), 8.13 (d, J=7.92 Hz, 1H).

Example 33

Methyl 6-Phenyl-5-(4-propylphenyl)-pyridine-2-carboxylate (Compound 33). Following General Procedure E, ethyl 6-phenyl-5-(4-propylphenyl)-pyridine-2-carboxylate (Compound 24, 67 mg, 0.19 mmol) and conc. $H_2SO_4$ (3 drops) in MeOH (3 ml) were reacted to produce the title compound as a white solid.

$^1$H NMR (300 MHz, CDCl$_3$) δ 0.93 (t, J=7.33 Hz, 3H), 1.56-1.71 (m, 2H), 2.51-2.63 (m, 2H), 4.02 (s, 3H), 7.01-7.13 (m, 4H), 7.16-7.31 (m, 3H), 7.34-7.43 (m, 2H), 7.85 (d, J=7.92 Hz, 1H), 8.14 (d, J=7.92 Hz, 1H).

Example 34

Methyl 6-Phenyl-5-(4-trifluoromethylphenyl)-pyridine-2-carboxylate (Compound 34).

Following General Procedure E, ethyl 6-phenyl-5-(4-trifluoromethylphenyl)-pyridine-2-carboxylate (Compound 25, 110 mg, 0.29 mmol) and conc. $H_2SO_4$ (5 drops) in MeOH (5 ml) were reacted to produce the title compound as a white solid.

$^1$H NMR (300 MHz, CDCl$_3$) δ 4.03 (s, 3H), 7.08-7.22 (m, 3H), 7.29-7.37 (m, 2H), 7.51 (s, 4H), 7.90 (d, J=7.92 Hz, 1H), 8.20 (d, J=7.92 Hz, 1H).

Example 35

Methyl 5-Phenyl-6-(4-trifluoromethylphenyl)-pyridine-2-carboxylate (Compound 35). Following General Procedure E, ethyl 5-phenyl-6-(4-trifluoromethylphenyl)-pyridine-2-carboxylate (Compound 29, 103 mg, 0.28 mmol) and conc. $H_2SO_4$ (5 drops) in MeOH (5 ml) were reacted to produce the title compound as a white solid.

$^1$H NMR (300 MHz, CDCl$_3$) δ 4.03 (s, 3H), 7.21-7.40 (m, 7H), 7.55 (d, J=8.50 Hz, 2H), 7.86 (d, J=7.92 Hz, 1H), 8.18 (d, J=7.92 Hz, 1H).

Example 36

Methyl 5-(4-Ethylphenyl)-3-methyl-6-phenylpyridine-2-carboxylate (Compound 36). Following General Procedure E, ethyl 5-(4-ethylphenyl)-3-methyl-6-phenylpyridine-2-carboxylate (Compound 26, 29 mg, 0.08 mmol) and conc. $H_2SO_4$ (3 drops) in MeOH (5 ml) were reacted to produce the title compound as an oil.

$^1$H NMR (500 MHz, CDCl$_3$) δ 1.23 (t, J=7.57 Hz, 3H), 2.58-2.68 (m, 5H), 3.99 (s, 3H), 7.05-7.13 (m, 4H), 7.18-7.25 (m, 3H), 7.34-7.40 (m, 2H), 7.61 (s, 1H).

Scheme 2

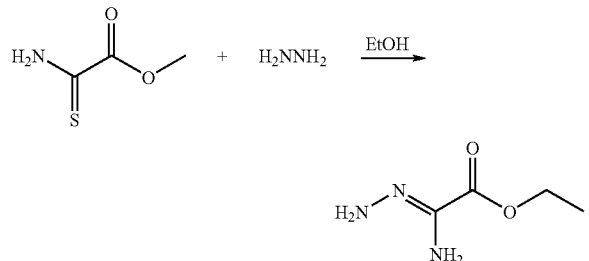

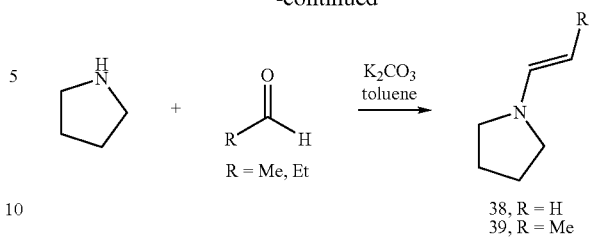

Example 37

Ethyl oxalamidrazonate (Compound 37). A solution of anhydrous hydrazine (0.5 ml, 15.0 mmol) in ethanol (5 ml) was added dropwise to a stirred solution of ethyl thiooxamate (2 g, 15.0 mmol) in ethanol (45 ml) under argon at room temperature. The mixture was stirred at room temperature for 1 hour, and the solvent was removed in vacuo and dried under high vacuum to get a white solid which was maintained in argon atmosphere after drying. The white solid was used in the next step without further purification.

Example 38

1-vinylpyrrolidine (Compound 38). General Procedure F. To a suspension of $K_2CO_3$ (3.8 g, 28.1 mmol) and pyrrolidine (1 g, 14.0 mmol) in toluene (10 ml) was added acetylaldehyde under argon at 0° C. The mixture was stirred at room temperature overnight. After filtration, the filtrate was concentrated in vacuo to yield a crude oil which was used in the next reaction without further purification.

Example 39

1-Propenylpyrrolidine (Compound 39). Following General Procedure F, $K_2CO_3$ (3.8 g, 28.1 mmol), pyrrolidine (1 g, 14.0 mmol) and propionaldehyde (1.6 g, 28.1 mmol) in toluene (10 ml) were reacted to produce the title compound as a brown oil.

Example 40

(E)-3-(4-ethylphenyl)prop-2-en-1-ol (Compound 40). General Procedure G. A solution of ethyl chloroformate (1.1 ml, 11.4 mmol) in THF (5 ml) was added to a solution of 4-ethylcinnamic acid (2 g, 11.4 mmol) and triethylamine (1.6 ml, 11.4 mmol) in THF (50 ml) at −5° C. to −10° C., and the solution was stirred for 30 min. The resulting white precipitate was filtered off, rinsed with THF (10 ml), and the combined filtrates were added to a solution of NaBH$_4$ (945 mg, 24.9 mmol) in H$_2$O (20 ml) slowly in order to maintain an internal temperature of 10° C. to 15° C. After the addition was completed, the reaction was stirred at room temperature for 4 hours, and then it was made acidic with HCl (20%). The layers were separated, and the aqueous layer was extracted with ethyl acetate. The combined organic layers were washed with NaHCO$_3$ (aq), and water, and brine, and dried over Na$_2$SO$_4$. The filtered solution was concentrated in vacuo, and the residue was purified by column chromatography (20% ethyl acetate in hexane) to yield a white solid.

$^1$H NMR (500 MHz, CDCl$_3$): δ ppm 1.23 (t, J=7.32 Hz, 3H), 2.64 (q, J=7.32 Hz, 2H), 4.31 (s, 2H), 6.30-6.39 (m, 1H), 6.61 (d, J=16.11 Hz, 1H), 7.16 (d, J=8.30 Hz, 2H), 7.32 (d, J=8.30 Hz, 2H).

Scheme 3

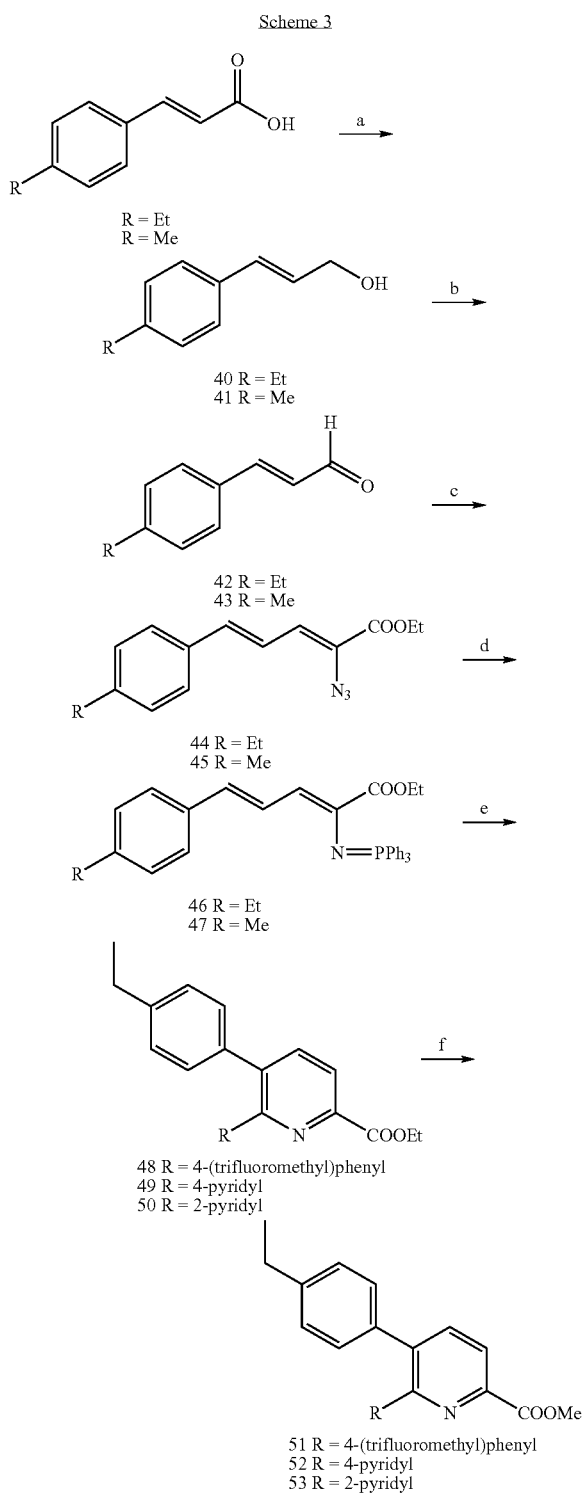

(a) i) Ethyl chloroformate, TEA, THF, ii) NaBH₄, H₂O, THF; (b) (COCl)₂, DMSO, TEA, -60° C.; (c) ethyl azidoacetate, NaOEt, EtOH; (d) PPh₃, ether; (e) R'CHO, CH₃CN, 60° C.; (f) MeOH, c.H₂SO₄, 60° C.

Example 41

(E)-3-(4-methylphenyl)prop-2-en-1-ol (Compound 41). Following General Procedure G, ethyl chloroformate (1.2 ml, 12.3 mmol), 4-methylcinnamic acid (2 g, 12.3 mmol) and triethylamine (1.7 ml, 12.3 mmol) in THF (50 ml) were reacted to produce a mixed anhydride, which was then were reacted with NaBH₄ (1.02 g, 27.2 mmol) in H₂O (20 ml) to produce title compound as a white solid.

$^1$H NMR (500 MHz, CDCl₃): δ ppm 2.34 (s, 3H), 4.31 (t, J=4.88 Hz, 2H), 6.30-6.39 (m, 1H), 6.61 (d, J=16.11 Hz, 1H), 7.14 (d, J=8.30 Hz, 2H), 7.29 (d, J=8.30 Hz, 2H).

Example 42

(E)-3-(4-ethylphenyl)acrylaldehyde (Compound 42). General Procedure H. To a solution of oxalyl chloride (5.9 ml, 11.8 mmol, 2 M in CH₂Cl₂) in CH₂Cl₂ (20 ml) was added a solution of DMSO (1.1 ml, 15.7 mmol) in CH₂Cl₂ (3 ml) dropwise at −60° C. A solution of (E)-3-(4-ethylphenyl)prop-2-en-1-ol (Compound 40, 1.3 g, 7.8 mmol) in CH₂Cl₂ (5 ml) was cannulated slowly into the above mixture at −60° C. After the reaction was stirred at the same temperature for 1 hour, a solution of triethylamine (4.4 ml, 31.4 mmol) in CH₂Cl₂ (5 ml) was added into the reaction, which was stirred an additional 1 hour at −60° C. The reaction was quenched with water, and the products were extracted with CH₂Cl₂. The organic layer was washed with 5% aqueous NaHCO₃, and brine, and dried over MgSO₄. The filtered solution was concentrated in vacuo, and the residue was purified by column chromatography (silica gel, 15% ethyl acetate in hexane) to obtain the title compound as a clear oil.

$^1$H NMR (500 MHz, CDCl₃): δ ppm 1.26 (t, J=7.32 Hz, 3H), 2.70 (q, J=7.32 Hz, 2H), 6.72 (dd, J=7.81, 16.11 Hz, 1H), 7.28 (d, J=8.30 Hz, 2H), 7.48 (d, J=15.62 Hz, 1H), 7.50 (d, J=8.30 Hz, 2H), 9.70 (s, 1H).

Example 43

(E)-3-(4-methylphenyl)acrylaldehyde (Compound 43). Following General Procedure H, oxalyl chloride (7.1 ml, 14.2 mmol, 2 M in CH₂Cl₂), DMSO (1.3 ml, 18.9 mmol), (E)-3-(4-methylphenyl)prop-2-en-1-ol (Compound 41, 1.4 g, 9.5 mmol) and triethylamine (4.4 ml, 31.4 mmol) in CH₂Cl₂ (5 ml) were reacted to obtain the title compound as an oil.

$^1$H NMR (500 MHz, CDCl₃): δ 2.40 (s, 3H), 6.72 (dd, J=7.81, 16.11 Hz, 1H), 7.25 (d, J=7.81 Hz, 2H), 7.44 (d, J=16.11 Hz, 1H), 7.48 (d, J=8.30 Hz, 2H), 9.70 (s, 1H).

Example 44

Ethyl (2Z,4E)-2-azido-5-(4-ethylphenyl)penta-2,4-dienoate (Compound 44). General Procedure I. A solution of NaOEt in ethanol was prepared in situ by dissolving Na (948 mg, 41.3 mmol) in 30 ml of ethanol. To this solution was added a solution of (E)-3-(4-ethylphenyl)acrylaldehyde (Compound 42, 1.1 g, 6.9 mmol) and ethyl azidoacetate (13 ml, 41.3 mmol) in EtOH (20 ml) dropwise at −10° C. After the addition was complete, the solution was stirred for an additional 1 hour at −10° C. The reaction was quenched by adding water, and the product was extracted with ethyl acetate. The organic phase was washed with water, and brine, and dried over Mg₂SO₄. The solvent was removed in vacuo, and the residue was purified by column chromatography (silica gel, 20% ethyl acetate in hexane) to obtain the title compound as a pale solid.

$^1$H NMR (500 MHz, CDCl₃): δ 1.24 (t, J=7.81 Hz, 3H), 1.37 (t, J=7.32 Hz, 3H), 2.66 (q, J=7.81 Hz, 2H), 4.34 (q, J=7.32 Hz, 2H), 6.76 (d, J=11.23 Hz, 1H), 6.81 (d, J=16.11 Hz, 1H), 7.15 (dd, J=11.23, 15.62 Hz, 1H), 7.19 (d, J=8.30 Hz, 2H), 7.39 (d, J=8.30 Hz, 2H).

Example 45

Ethyl (2Z,4E)-2-azido-5-(4-methylphenyl)penta-2,4-dienoate (Compound 45). Following General Procedure I, a 1.38 M solution of NaOEt in ethanol (30 ml), (E)-3-(4-methylphenyl)acrylaldehyde (Compound 43, 1.1 g, 7.5 mmol) and ethyl azidoacetate (12 ml, 37.5 mmol) in EtOH (20 ml) were reacted to produce the title compound as a solid.

$^1$H NMR (500 MHz, CDCl$_3$): δ 1.37 (t, J=7.32 Hz, 3H), 2.36 (s, 3H), 4.34 (q, J=7.32 Hz, 2H), 6.76 (d, J=10.25 Hz, 1H), 6.81 (d, J=15.62 Hz, 1H), 7.11 (dd, J=11.23, 15.62 Hz, 1H), 7.17 (d, J=8.30 Hz, 2H), 7.39 (d, J=7.81 Hz, 2H).

Example 46

3-Ethoxycarbonyl-1,1,1-triphenyl-6-(4-ethylphenyl)-2-aza-1λ$^5$-phosphahexa-1,3,5-triene (Compound 46). General Procedure J. A solution of triphenylphosphine (1.2 g, 4.54 mmol) in diethyl ether (10 ml) was added dropwise to a solution of ethyl (2Z,4E)-2-azido-5-(4-ethylphenyl)penta-2,4-dienoate (Compound 44, 1.2 g, 4.54 mmol) in diethyl ether (20 ml) at 0° C. The solution was stirred for 12 hours at room temperature. Evaporation of solvent afforded a crude yellow solid, which was purified by column chromatography (silica gel, 20% ethyl acetate in hexane) to give the title compound.

$^1$H NMR (500 MHz, CDCl$_3$): δ 1.04 (t, J=7.81 Hz, 3H), 1.23 (t, J=7.32 Hz, 3H), 2.62 (q, J=7.81 Hz, 2H), 3.89 (q, J=7.32 Hz, 2H), 6.60 (d, J=15.62 Hz, 1H), 6.70 (dd, J=3.91, 10.74 Hz, 1H), 7.12 (d, J=8.30 Hz, 2H), 7.30 (d, J=8.30 Hz, 2H), 7.41-7.50 (m, 9H), 7.66 (dd, J=11.23, 15.62 Hz, 1H), 7.73-7.77 (m, 6H).

Example 47

3-Ethoxycarbonyl-1,1,1-triphenyl-6-(4-methylphenyl)-2-aza-1λ$^5$-phosphahexa-1,3,5-triene (Compound 47). Following General Procedure J, triphenylphosphine (1.5 g, 5.8 mmol) ethyl (2Z,4E)-2-azido-5-(4-methylphenyl)penta-2,4-dienoate (Compound 45, 1.5 g, 5.8 mmol) in diethyl ether (50 ml) were reacted to produce the title compound as a yellow solid.

$^1$H NMR (500 MHz, CDCl$_3$): δ 1.04 (t, J=7.32 Hz, 3H), 2.33 (s, 3H), 3.89 (q, J=7.32 Hz, 2H), 6.60 (d, J=16.11 Hz, 1H), 6.70 (dd, J=3.91, 11.23 Hz, 1H), 7.09 (d, J=8.30 Hz, 2H), 7.27 (d, J=8.30 Hz, 2H), 7.41-7.50 (m, 9H), 7.66 (dd, J=11.23, 16.11 Hz, 1H), 7.73-7.77 (m, 6H).

Example 48

Ethyl 5-(4-ethylphenyl)-6-(4-(trifluoromethyl)phenyl)pyridine-2-carboxylate (Compound 48). General Procedure K. 4-(trifluoromethyl)benzaldehyde (153 mg, 1.88 mmol) was added to a stirred solution of 3-ethoxycarbonyl-1,1,1-triphenyl-6-(4-ethylphenyl)-2-aza-1λ$^5$-phosphahexa-1,3,5-triene (Compound 46, 444 mg, 0.88 mmol) in dry acetonitrile (10 ml) and the solution was heated to 60° C. for 18 hours. The solution was concentrated in vacuo, and the crude product was passed through a silica gel column with 15% ethyl acetate in hexane as eluant to give the title compound as a yellow oil.

$^1$H NMR (500 MHz, CDCl$_3$): δ 1.24 (t, J=7.81 Hz, 3H), 1.46 (t, J=7.32 Hz, 3H), 2.67 (q, J=7.81 Hz, 2H), 4.51 (q, J=7.32 Hz, 2H), 7.09 (d, J=8.30 Hz, 2H), 7.16 (d, J=8.30 Hz, 1H), 7.49-7.55 (m, 4H), 7.88 (d, J=7.81 Hz, 1H), 8.16 (d, J=7.81 Hz, 1H).

Example 49

Ethyl 3-(4-Ethylphenyl)-[2,4']-bipyridinyl-6-carboxylate (Compound 49). Following General Procedure K, 4-pyridinecarboxaldehyde (92 mg, 0.86 mmol) and 3-ethoxycarbonyl-1,1,1-triphenyl-6-(4-ethylphenyl)-2-aza-1λ$^5$-phosphahexa-1,3,5-triene (Compound 46, 434 mg, 0.86 mmol) in dry acetonitrile (10 ml) were reacted to produce the title compound as a yellow solid.

$^1$H NMR (500 MHz, CDCl$_3$): δ 1.24 (t, J=7.81 Hz, 3H), 1.46 (t, J=7.32 Hz, 3H), 2.67 (q, J=7.81 Hz, 2H), 4.51 (q, J=7.32 Hz, 2H), 7.09 (d, J=8.30 Hz, 2H), 7.16 (d, J=8.30 Hz, 1H), 7.33 (dd, J=1.46, 4.39 Hz, 2H), 7.90 (d, J=7.81 Hz, 1H), 8.21 (d, J=7.81 Hz, 1H), 8.52 (dd, J=1.46, 4.39 Hz, 2H).

Example 50

Ethyl 3-(4-Ethylphenyl)-[2,2']-bipyridinyl-6-carboxylate (Compound 50). Following General Procedure K, 2-pyridinecarboxaldehyde (41 mg, 0.38 mmol) and 3-ethoxycarbonyl-1,1,1-triphenyl-6-(4-ethylphenyl)-2-aza-1λ$^5$-phosphahexa-1,3,5-triene (Compound 46, 193 mg, 0.38 mmol) in dry acetonitrile (5 ml) were reacted to produce the title compound as a yellow solid.

$^1$H NMR (500 MHz, CDCl$_3$): δ 1.22 (t, J=7.81 Hz, 3H), 1.45 (t, J=7.32 Hz, 3H), 2.62 (q, J=7.81 Hz, 2H), 4.52 (q, J=7.32 Hz, 2H), 7.05-7.11 (m, 4H), 7.17-7.20 (m, 1H), 7.49 (dd, J=0.98, 7.81 Hz, 1H), 7.58-7.62 (m, 1H), 7.92 (d, J=7.81 Hz, 1H), 8.20 (d, J=7.81 Hz, 1H), 8.50-8.55 (m, 1H).

Example 51

Methyl 5-(4-Ethylphenyl)-6-(4-(trifluoromethyl)phenyl)pyridine-2-carboxylate (Compound 51). Following General Procedure E, ethyl 5-(4-ethylphenyl)-6-(4-(trifluoromethyl)phenyl)pyridine-2-carboxylate (Compound 48, 60 mg, 0.15 mmol) and conc. H$_2$SO$_4$ (10 drops) in methanol were reacted to produce the title compound as a light yellow solid.

$^1$H NMR (500 MHz, CDCl$_3$): δ ppm 1.24 (t, J=7.81 Hz, 3H), 2.67 (q, J=7.81 Hz, 2H), 4.03 (s, 3H), 7.09 (d, J=8.30 Hz, 2H), 7.16 (d, J=8.30 Hz, 1H), 7.49-7.55 (m, 4H), 7.89 (d, J=7.81 Hz, 1H), 8.18 (d, J=7.81 Hz, 1H).

Example 52

Methyl 5-(4-Ethylphenyl)-6-(pyridin-4-yl)pyridine-2-carboxylate (Compound 52). Following General Procedure E, ethyl 5-(4-ethylphenyl)-6-(pyridine-4-yl)phenyl)pyridine-2-carboxylate (Compound 49, 48 mg, 0.14 mmol) and conc. H$_2$SO$_4$ (10 drops) in methanol were reacted to produce the title compound as a light yellow solid.

$^1$H NMR (500 MHz, CDCl$_3$): δ ppm 1.24 (t, J=7.81 Hz, 3H), 2.65 (q, J=7.81 Hz, 2H), 4.03 (s, 3H), 7.09 (d, J=7.81 Hz, 2H), 7.16 (d, J=7.81 Hz, 1H), 7.32 (dd, J=1.46, 4.39 Hz, 2H), 7.90 (d, J=8.30 Hz, 1H), 8.21 (d, J=8.30 Hz, 1H), 8.52 (dd, J=1.46, 4.39 Hz, 2H).

Example 53

Methyl 5-(4-ethylphenyl)-6-(pyridin-2-yl)pyridine-2-carboxylate (Compound 53). Following General Procedure E, ethyl 5-(4-ethylphenyl)-6-(pyridine-2-yl)phenyl)pyridine-2-carboxylate (Compound 50, 16 mg, 0.05 mmol) and conc. H$_2$SO$_4$ (10 drops) in methanol were reacted to produce the title compound as a light yellow solid.

$^1$H NMR (500 MHz, CDCl$_3$): δ ppm 1.22 (t, J=7.81 Hz, 3H), 2.63 (q, J=7.81 Hz, 2H), 4.02 (s, 3H), 7.05-7.11 (m, 4H), 7.18-7.22 (m, 1H), 7.42 (dd, J=0.98, 7.81 Hz 1H), 7.56-7.63 (m, 1H), 7.93 (d, J=8.30 Hz, 1H), 8.23 (d, J=8.30 Hz, 1H), 8.55-8.57 (m, 1H).

Example 54

5,6-diphenylpyridine-2-carbaldehyde (Compound 54). General Procedure L. To a solution of ethyl 5,6-diphenylpyridine-2-carboxylate (Compound 21, 145 mg, 0.48 mmol) in CH$_2$Cl$_2$ (5 ml) at −78° C. was added DIBAL-H (0.72 ml, 0.72 mmol, 1.0 M in Toluene) and the mixture was stirred between −78° C. and −60° C. for 1 hour under argon. The reaction was quenched with aq, NH$_4$Cl, diethyl ether and 400 mg Celite were added, and the mixture was stirred at room temperature 30 min. The solid was filtered off and rinsed with ether, and the combined filtrate was concentrated in vacuo, and the residue was purified by column chromatography (silica gel, 15% ethyl acetate in hexane) to produce the title compound.

$^1$H NMR (500 MHz, CDCl$_3$) δ 7.17-7.22 (m, 2H), 7.27-7.32 (m, 6H), 7.40-7.43 (m, 2H), 7.92 (d, J=7.91 Hz, 1H), 8.01 (d, J=7.91 Hz, 1H), 10.19 (s, 1H).

Compound 55: $^1$H NMR (500 MHz, CDCl$_3$): δ 2.38 (s, 3H), 7.08-7.18 (m, 4H), 7.29-7.38 (m, 3H, 7.42-7.52 (m, 2H), 7.94 (d, J=7.32 Hz, 1H), 8.03 (d, J=7.81 Hz, 1H), 10.27 (s, 1H).

Compound 60: $^1$H NMR (300 MHz, CDCl$_3$): δ 2.34 (s, 3H), 4.84 (s, 2H), 7.02-7.13 (m, 4H), 7.21-7.31 (m, 4H), 7.35-7.42 (m, 2H), 7.71 (d, J=7.62 Hz, 1H).

Example 56 and Example 61

5-(4-Ethylphenyl)-6-phenylpyridine-2-carbaldehyde (Compound 56) and [5-(4-Ethylphenyl)-6-phenylpyridin-2-yl]-methanol (Compound 61). Following General Procedure L, ethyl 5-(4-ethylphenyl)-6-phenylpyridine-2-carboxylate (Compound 23, 200 mg, 0.60 mmol) and DIBAL-H (1.2 ml, 1.20 mmol, 1.0 M in CH$_2$Cl$_2$) in CH$_2$Cl$_2$ (5 ml) were reacted

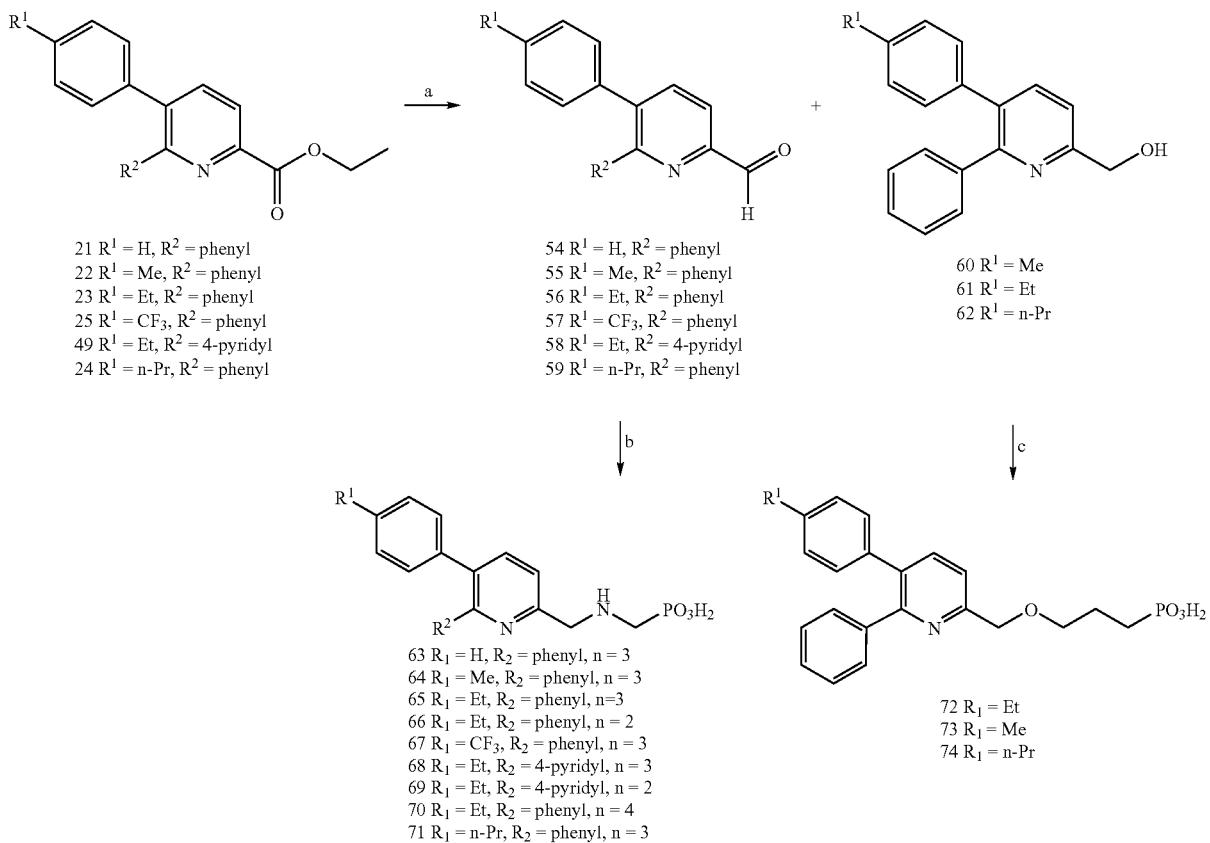

Scheme 4

(a) DiBAL-H, CH$_2$Cl$_2$, -78° C. to -60° C.; (b) n-Bu$_4$NOH, NH$_2$(CH$_2$)$_n$PO$_3$H$_2$, MeOH, Na(BH$_3$)CN, 50° C.; (c)i) NaH, Br(CH$_2$)$_3$PO(OEt)$_2$, DMF, 110° C.; ii) TMSI, CHCl$_3$.

Example 55 and Example 60

6-Phenyl-5-p-tolylpyridine-2-carbaldehyde (Compound 55) and (6-phenyl-5-p-tolylpyridin-2-yl)methanol (Compound 60). Following General Procedure L, ethyl 6-phenyl-5-p-tolylpyridine-2-carboxylate (Compound 22, 1.1 g, 3.47 mmol) and DIBAL-H (5.2 ml, 5.21 mmol, 1.0M in cyclohexane) in CH$_2$Cl$_2$ (30 ml) were reacted to produce Compound 55 and Compound 60 after separation by column chromatography (silica gel, 15% ethyl acetate in hexane).

to produce Compound 56 and Compound 61 after separation by column chromatography (silica gel, 15% ethyl acetate in hexane).

Compound 56: $^1$H NMR (500 MHz, CDCl$_3$): δ 1.27 (t, J=7.81 Hz, 3H), 2.67 (q, J=7.81 Hz, 2H), 7.13-7.17 (m, 4H), 7.30-7.34 (m, 3H), 7.44-7.47 (m, 2H), 7.93 (d, J=7.81 Hz, 1H), 8.02 (d, J=7.81 Hz, 1H), 10.23 (s, 1H).

Compound 61: $^1$H NMR (300 MHz, CDCl$_3$): δ ppm 1.24 (t, J=7.81 Hz, 3H), 2.66 (q, J=7.81 Hz, 2H), 4.85 (d, J=3.42 Hz, 2H), 7.08-7.13 (m, 4H), 7.25-7.28 (m, 5H), 7.39 (d, J=7.81 Hz, 1H), 7.74 (d, J=7.81 Hz, 1H).

Example 57

5-(4-Trifluoromethylphenyl)-6-phenylpyridine-2-carbaldehyde (Compound 57). Following General Procedure L, ethyl 5-(4-trifluoromethylphenyl)-6-phenylpyridine-2-carboxylate (Compound 25, 74 mg, 0.20 mmol) and DIBAL-H (0.3 ml, 0.30 mmol, 1.0 M in hexane) in $CH_2Cl_2$ (3 ml) were reacted to produce the title compound after purification by column chromatography (silica gel, 15% ethyl acetate in hexane).

$^1$H NMR (300 MHz, $CDCl_3$) δ 7.29-7.39 (m, 2H), 7.45-7.62 (m, 4H), 7.95 (d, J=7.92 Hz, 1H), 8.05 (d, J=7.92 Hz, 1H), 10.19 (s, 1H).

Example 58

3-(4-Ethylphenyl)-[2,4']-bipyridinyl-6-carbaldehyde (Compound 58) Following General Procedure L, ethyl 3-(4-ethylphenyl)-[2,4']-bipyridinyl-6-carboxylate (Compound 49, 164 mg, 0.49 mmol) and DIBAL-H (0.75 ml, 0.75 mmol, 1.0 M in $CH_2Cl_2$) in $CH_2Cl_2$ (5 ml) were reacted to produce the title compound after purification by column chromatography (silica gel, 15% ethyl acetate in hexane).

$^1$H NMR (300 MHz, $CDCl_3$): δ 1.25 (t, J=7.81 Hz, 3H), 2.68 (q, J=7.81 Hz, 2H), 7.11 ((d, J=8.30 Hz, 2H), 7.18 (d, J=7.81 Hz, 1H), 7.34 (dd, J=1.95, 4.39 Hz, 2H), 7.94 (d, J=7.32 Hz, 1H), 8.06 (d, J=7.81 Hz, 1H), 8.56 (dd, J=1.95, 4.39 Hz, 2H), 10.17 (s, 1H).

Example 59 and Example 62

6-Phenyl-5-(4-propylphenyl)pyridine-2-carbaldehyde (Compound 59) and (6-Phenyl-5-(4-propylphenyl)pyridin-2-yl)methanol (Compound 62). Following General Procedure L, ethyl 6-phenyl-5-(4-propyl-phenyl)-pyridine-2-carboxylate (Compound 24, 370 mg, 0.49 mmol) and DIBAL-H (2.1 ml, 2.1 mmol, 1.0 M in cyclohexane) in $CH_2Cl_2$ (5 ml) were reacted to produce Compound 59 and Compound 62 after separation by column chromatography (silica gel, 15% ethyl acetate in hexane).

Compound 59: $^1$H NMR (500 MHz, $CDCl_3$): δ 0.94 (t, J=7.32 Hz, 3H), 1.59-1.71 (m, 2H), 2.54-2.62 (m, 2H), 7.11 (s, 4H), 7.26-7.35 (m, 3H), 7.40-7.45 (m, 2H), 7.91 (d, J=7.81 Hz, 1H), 7.99 (d, J=7.81 Hz, 1H), 10.19 (s, 1H).

Compound 62: $^1$H NMR (500 MHz, $CDCl_3$): δ 0.94 (t, J=7.32 Hz, 3H), 1.60-1.70 (m, 2H), 2.54-2.62 (m, 2H), 4.87 (s, 2H), 7.04-7.13 (m, 4H), 7.22-7.32 (m, 4H), 7.40 (d, J=7.32 Hz, 2H), 7.77 (d, J=7.81 Hz, 1H).

Example 63

{3-[(5,6-Diphenylpyridin-2-ylmethyl)-amino]-propyl}-phosphonic Acid (Compound 63). General Procedure M. To a solution of 5,6-diphenylpyridine-2-carbaldehyde (Compound 54, 95 mg, 0.37 mmol) and (3-amino-propyl)-phosphonic acid (51 mg, 0.37 mmol) in MeOH (3 ml) was added $Bu_4NOH$ (0.4 ml, 0.37 mmol, 1M in MeOH) under argon. The mixture was stirred at 50° C. for 30 min. before adding $NaCNBH_3$ (23 mg, 0.37 mmol) to the mixture. The solution was stirred at 50° C. for 3 hours, and then it was concentrated in vacuo. The resulting crude solid was purified MPLC column chromatography (silica gel, 0-100% MeOH in ethyl acetate) to obtain the title compound as a white solid.

$^1$H NMR (300 MHz, $CDCl_3$): δ 1.69-1.76 (m, 2H), 2.00-2.08 (m, 2H), 3.09 (t, J=6.95 Hz, 2H), 4.19 (s, 2H), 7.02-7.09 (m, 2H), 7.19-7.26 (m, 5H), 7.30-7.36 (m, 3H), 7.60-7.72 (m, 2H).

Example 64

{3-[(6-Phenyl-5-p-tolylpyridin-2-ylmethyl)-amino]-propyl}-phosphonic Acid (Compound 64). Following General Procedure M, 6-phenyl-5-p-tolylpyridine-2-carbaldehyde (Compound 55, 67 mg, 0.25 mmol), (3-aminopropyl)-phosphonic acid (34 mg, 0.25 mmol), $Bu_4NOH$ (0.2 ml, 0.25 mmol, 1 M in MeOH) and $NaCNBH_3$ (15 mg, 0.25 mmol) in MeOH (3 ml) were reacted to produce the title compound as a white solid.

$^1$H NMR (500 MHz, $CD_3OD$): δ 1.69-1.76 (m, 2H), 2.00-2.08 (m, 2H), 2.34 (s, 3H), 3.19 (t, J=6.80 Hz, 2H), 4.39 (s, 2H), 7.08-7.16 (m, 4H), 7.25-7.31 (m, 3H), 7.39-7.42 (m, 2H), 7.54 (d, J=7.80 Hz, 1H), 7.89 (d, J=7.81 Hz, 1H).

Example 65

3-{[5-(4-Ethylphenyl)-6-phenylpyridin-2-ylmethyl]-amino}-propyl)-phosphonic Acid (Compound 65). Following General Procedure M, 5-(4-ethylphenyl)-6-phenylpyridine-2-carbaldehyde (Compound 56, 43 mg, 0.15 mmol), (3-aminopropyl)-phosphonic acid (21 mg, 0.15 mmol), $Bu_4NOH$ (0.15 ml, 0.15 mmol, 1 M in MeOH) and $NaCNBH_3$ (9 mg, 0.15 mmol) in MeOH (3 ml) were reacted to produce the title compound as a white solid.

$^1$H NMR (500 MHz, $CD_3OD$): δ 1.24 (t, J=7.81 Hz, 3H), 1.69-1.75 (m, 2H), 2.00-2.08 (m, 2H), 2.66 (q, J=7.81 Hz, 2H), 3.19 (t, J=6.35 Hz, 2H), 4.36 (s, 2H), 7.10-7.16 (m, 4H), 7.25-7.31 (m, 3H), 7.39-7.42 (m, 2H), 7.54 (d, J=8.30 Hz, 1H), 7.88 (d, J=7.81 Hz, 1H).

Example 66

(2-{[5-(4-Ethyl-phenyl)-6-phenyl-pyridin-2-ylmethyl]-amino}-ethyl)-phosphonic Acid (Compound 66). Following General Procedure M, 5-(4-ethyl-phenyl)-6-phenyl-pyridine-2-carbaldehyde (Compound 56, 31 mg, 0.11 mmol), (3-amino-ethyl)-phosphonic acid (14 mg, 0.11 mmol), $Bu_4NOH$ (0.11 ml, 0.11 mmol, 1 M in MeOH) and $NaCNBH_3$ (7 mg, 0.11 mmol) in MeOH (2 ml) were reacted to produce the title compound as a white solid.

$^1$H NMR (500 MHz, $CD_3OD$): δ 1.23 (t, J=7.81 Hz, 3H), 1.90-1.96 (m, 2H), 2.66 (q, J=7.81 Hz, 2H), 3.19 (t, J=6.35 Hz, 2H), 4.34 (s, 2H), 7.09-7.16 (m, 4H), 7.25-7.29 (m, 3H), 7.39-7.42 (m, 2H), 7.53 (d, J=7.81 Hz, 1H), 7.87 (d, J=8.30 Hz, 1H).

Example 67

(3-{[6-Phenyl-5-(4-trifluoromethylphenyl)-pyridin-2-ylmethyl]-amino}-propyl)-phosphonic Acid (Compound 67). Following General Procedure M, 5-(4-trifluoromethylphenyl)-6-phenyl-pyridine-2-carbaldehyde (Compound 57, 58 mg, 0.18 mmol), (3-amino-propyl)-phosphonic acid (25 mg, 0.18 mmol), $Bu_4NOH$ (0.18 ml, 0.18 mmol, 1 M in MeOH) and $NaCNBH_3$ (11 mg, 0.18 mmol) in MeOH (3 ml) were reacted to produce the title compound as a white solid.

$^1$H NMR (500 MHz, $CD_3OD$): δ 1.02 (t, J=7.33 Hz, 3H), 1.65-1.75 (m, 2H), 1.95-2.08 (m, 2H), 3.16 (t, J=6.35 Hz, 2H), 4.36 (s, 2H), 7.16-7.21 (m, 2H), 7.29-7.31 (m, 3H), 7.52-7.59 (m, 5H), 7.91 (d, J=7.92 Hz, 1H).

Example 68

(3-{[3-(4-Ethylphenyl)-[2,4']-bipyridin-6-ylmethyl]-amino}-propyl)-phosphonic Acid (Compound 68). Following General Procedure M, 3-(4-ethyl-phenyl)-[2,4']-bipyridinyl-6-carbaldehyde (Compound 58, 50 mg, 0.17 mmol), (3-amino-propyl)-phosphonic acid (24 mg, 0.17 mmol), Bu$_4$NOH (0.17 ml, 0.17 mmol, 1 M in MeOH) and NaCNBH$_3$ (11 mg, 0.17 mmol) in MeOH (3 ml) were reacted to produce the title compound as a white solid.

$^1$H NMR (500 MHz, CD$_3$OD): δ1.25 (t, J=7.81 Hz, 3H), 1.69-1.79 (m, 2H), 2.00-2.09 (m, 2H), 2.66 (q, J=7.81 Hz, 2H), 3.17 (t, J=6.83 Hz, 2H), 4.37 (s, 2H), 7.16 (d, J=8.30 Hz, 2H), 7.22 (d, J=8.30 Hz, 2H), 7.49 (dd, J=1.95, 4.88 Hz, 2H), 7.64 (d, J=7.81 Hz, 1H), 7.94 (d, J=7.81 Hz, 1H), 8.45 (dd, J=1.46, 4.39 Hz, 2H).

Example 69

(2-{[3-(4-Ethyl-phenyl)-[2,4']-bipyridinyl-6-ylmethyl]-amino}-ethyl)-phosphonic Acid (Compound 69). Following General Procedure M, 3-(4-ethyl-phenyl)-[2,4']-bipyridinyl-6-carbaldehyde (Compound 58, 39 mg, 0.14 mmol), (3-amino-ethyl)-phosphonic acid (17 mg, 0.14 mmol), Bu$_4$NOH (0.14 ml, 0.14 mmol, 1 M in MeOH) and NaCNBH$_3$ (9 mg, 0.14 mmol) in MeOH (3 ml) were reacted to produce the title compound as a white solid.

$^1$H NMR (500 MHz, CD$_3$OD): δ 1.25 (t, J=7.81 Hz, 3H), 1.90-1.99 (m, 2H), 2.69 (q, J=7.81 Hz, 2H), 3.30 (t, J=6.83 Hz, 2H), 4.39 (s, 2H), 7.14 (d, J=8.30 Hz, 2H), 7.20 (d, J=8.30 Hz, 2H), 7.48 (dd, J=1.46, 4.39 Hz, 2H), 7.62 (d, J=7.81 Hz, 1H), 7.93 (d, J=7.81 Hz, 1H), 8.45 (dd, J=1.95, 4.88 Hz, 2H).

Example 70

4-((5-(4-Ethylphenyl)-6-phenylpyridin-2-yl)methylamino)butylphosphonic Acid (Compound 70). Following General Procedure M, 5-(4-ethyl-phenyl)-6-phenyl-pyridine-2-carbaldehyde (Compound 56, 58 mg, 0.18 mmol), 4-aminobutylphosphonic acid (21 mg, 0.18 mmol), Bu$_4$NOH (0.18 ml, 0.18 mmol, 1 M in MeOH) and NaCNBH$_3$ (9 mg, 0.18 mmol) in MeOH (2 ml) were reacted to produce the title compound as a white solid.

$^1$H NMR (500 MHz, CD$_3$OD): δ 1.23 (t, J=7.81 Hz, 3H), 1.56-1.70 (m, 6H), 2.61-2.71 (m, 4H), 3.85 (s, 2H), 7.07-7.12 (m, 4H), 7.25-7.33 (m, 5H), 7.66 (d, J=8.30 Hz, 1H), 7.83 (d, J=8.30 Hz, 1H).

Example 71

3-((6-Phenyl-5-(4-propylphenyl)pyridin-2-yl)methylamino)propylphosphonic Acid (Compound 71). Following General Procedure M, 6-phenyl-5-(4-propylphenyl)pyridine-2-carbaldehyde (Compound 59, 74 mg, 0.25 mmol), (3-amino-propyl)phosphonic acid (34 mg, 0.25 mmol), Bu$_4$NOH (0.25 ml, 0.25 mmol, 1M in MeOH) and NaCNBH$_3$ (15 mg, 0.25 mmol) in MeOH (5 ml) were reacted to produce the title compound as a white solid.

$^1$H NMR (500 MHz, CD$_3$OD) δ 0.94 (t, J=7.32 Hz, 3H), 1.58-1.78 (m, 4H), 1.92-2.09 (m, 2H), 2.51-2.66 (m, 2H), 3.05 (t, J=6.59 Hz, 2H), 4.23 (s, 2H), 7.03-7.16 (m, 4H), 7.19-7.32 (m, 3H), 7.36-7.38 (m, 2H), 7.55 (d, J=7.81 Hz, 1H), 7.85 (d, J=8.30 Hz, 1H).

Example 72

{3-[5-(4-Ethyl-phenyl)-6-phenyl-pyridin-2-ylmethoxy]-propyl}-phosphonic Acid (Compound 72). General Procedure N. To a suspension of NaH (11 mg, 0.48 mmol) in DMF (1 ml) was added a solution of [5-(4-ethyl-phenyl)-6-phenyl-pyridin-2-yl]-methanol (Compound 61, 69 mg, 0.24 mmol) at 0° C. under argon. After the mixture was stirred for 30 min., a solution of (3-bromo-propyl)-phosphonic acid diethyl ester (123 mg, 0.48 mmol) was added into the mixture and the reaction was heated to 110° C. overnight. The reaction was quenched with water, and the products were extracted with ethyl acetate. The combined organic layers were washed with water, and brine, and dried over Na$_2$SO$_4$. The filtered solvents were concentrated in vacuo, and the residue was purified by MPLC on silica gel (0-100% ethyl acetate in hexane) to produce a crude mixture containing {3-[5-(4-Ethyl-phenyl)-6-phenyl-pyridin-2-ylmethoxy]-propyl}-phosphonic acid diethyl ester.

To a solution of crude {3-[5-(4-ethyl-phenyl)-6-phenyl-pyridin-2-ylmethoxy]-propyl}-phosphonic acid diethyl ester (18 mg, 0.039 mmol) in CHCl$_3$ (2 ml) at room temperature was added TMSI (77 mg, 0.39 mmol) dropwise. After the mixture was stirred for 1 hour, the solvent was removed in vacuo to recover a yellow oily residue. The residue was taken-up in THF/H$_2$O (4:1) and stirred at room temperature overnight. The mixture was extracted with ethyl acetate. The combined organic layers were washed with NaHSO$_3$, and water, and brine, and dried over Na$_2$SO$_4$. The filtered solvents were concentrated in vacuo and the residue was purified by MPLC on silica gel (0-100% MeOH in ethyl acetate) to give the title compound as a white solid.

$^1$H NMR (500 MHz, CD$_3$OD): δ1.20 (t, J=7.81 Hz, 3H), 1.67-1.73 (m, 2H), 1.90-2.01 (m, 2H), 2.61 (q, J=7.81 Hz, 2H), 3.67 (t, J=6.35 Hz, 2H), 4.69 (s, 2H), 7.04-7.10 (m, 4H), 7.23-7.29 (m, 5H), 7.59 (d, J=7.81 Hz, 1H), 7.84 (d, J=7.81 Hz, 1H).

Example 73

3-((6-Phenyl-5-p-tolylpyridin-2-yl)methoxy)propylphosphonic Acid (Compound 73). Following General Procedure N, NaH (17 mg, 0.67 mmol), [5-(4-methyl-phenyl)-6-phenyl-pyridin-2-yl]-methanol (Compound 60, 91 mg, 0.33 mmol) in DMF (3 ml) was refluxed to produce crude {3-[5-(4-methyl-phenyl)-6-phenyl-pyridin-2-ylmethoxy]-propyl}-phosphonic acid diethyl ester, which was then reacted with TMSI (0.13 ml, 0.09 mmol) in CHCl$_3$ (3 ml) to obtain the title compound as an oil.

$^1$H NMR (500 MHz, CD$_3$OD) δ 1.73-1.88 (m, 2H), 1.90-2.05 (m, 2H), 2.30 (s, 3H), 3.69 (t, J=6.35 Hz, 2H), 4.69 (s, 2H), 6.97-7.12 (m, 4H), 7.20-7.34 (m, 5H), 7.58 (d, J=8.30 Hz, 1H), 7.86 (d, J=8.30 Hz, 1H).

Example 74

3-((6-Phenyl-5-(4-propylphenyl)pyridin-2-yl)methoxy)propylphosphonic Acid (Compound 74). Following General Procedure N, NaH (17 mg, 0.67 mmol), [5-(4-methyl-phenyl)-6-phenyl-pyridin-2-yl]-methanol (Compound 62, 105 mg, 0.35 mmol) in DMF (3 ml) was refluxed to produce crude {3-[5-(4-n-propyl-phenyl)-6-phenyl-pyridin-2-ylmethoxy]-propyl}-phosphonic acid diethyl ester, which was then reacted with TMSI (0.13 ml, 0.09 mmol) in CHCl$_3$ (3 ml) to obtain the title compound as an oil.

Example 75

1-(5,6-Diphenyl-pyridin-2-yl)-ethanone (Compound 75). General Procedure O. To a solution of ethyl 5,6-diphenylpyridine-2-carboxylate (Compound 21, 246 mg, 0.81 mmol) in toluene (5 ml) was added N,N'-dimethylethylenediamine (DMEDA, 78.7 mg, 0.89 mmol) and trimethylaluminum (1.2 ml, 2.44 mmol, 2 M in toluene) dropwise under argon at room temperature. After the mixture was refluxed at 112° C. for 2.5 hours, it was quenched with water, and the products were extracted with ethyl acetate. The combined organic layers were washed with brine, and dried over $Na_2SO_4$. The filtered solvents were concentrated in vacuo, and the residue was purified by silica gel chromatography (15% ethyl acetate in hexane) to give title compound as a yellow solid.

$^1$H NMR (300 MHz, $CDCl_3$) δ 2.81 (s, 3H), 7.17-7.23 (m, 2H), 7.27-7.33 (m, 6H), 7.40-7.46 (m, 2H), 7.85 (d, J=7.92 Hz, 1H), 8.06 (d, J=8.21 Hz, 1H).

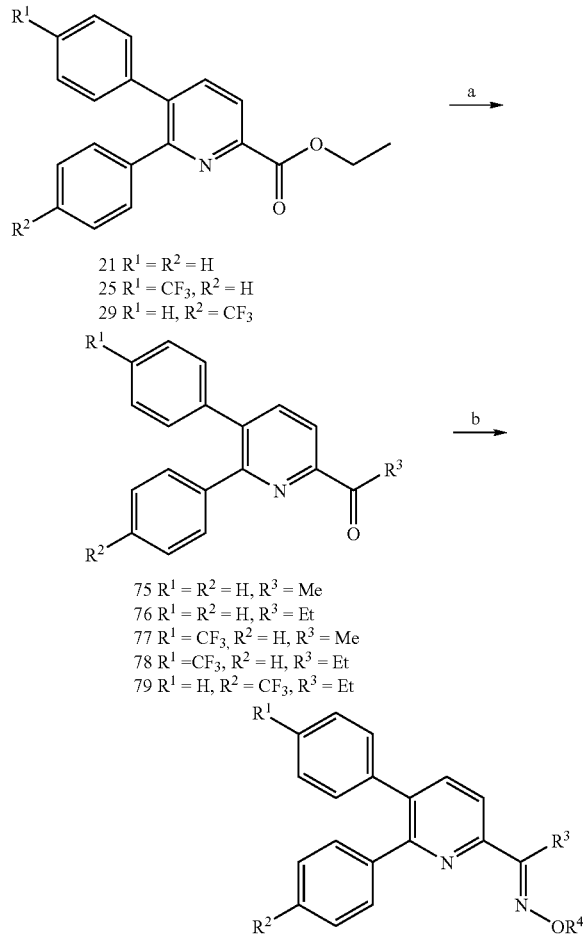

Scheme 5

21 $R^1 = R^2 = H$
25 $R^1 = CF_3, R^2 = H$
29 $R^1 = H, R^2 = CF_3$

75 $R^1 = R^2 = H, R^3 = Me$
76 $R^1 = R^2 = H, R^3 = Et$
77 $R^1 = CF_3, R^2 = H, R^3 = Me$
78 $R^1 = CF_3, R^2 = H, R^3 = Et$
79 $R^1 = H, R^2 = CF_3, R^3 = Et$

80 $R^1 = R^2 = R^4 = H, R^3 = Me$
81 $R^1 = R^2 = R^4 = H, R^3 = Et$
82 $R^1 = R^2 = H, R^3 = Me, R^4 = Me$
83 $R^1 = R^2 = H, R^3 = Et, R^4 = Me$
84 $R^1 = CF_3, R^2 = H, R^3 = Me, R^4 = Me$
85 $R^1 = CF_3, R^2 = H, R^3 = Et, R^4 = Me$ (a) $R_3Al$, DMEDA, Tol, 110° C.; (b) i) $NH_2OR_4$, EtOH, Pyridine, 70° C.

Example 76

1-(5,6-Diphenyl-pyridin-2-yl)-propan-1-one (Compound 76). Following General Procedure O, ethyl 5,6-diphenylpyridine-2-carboxylate (Compound 21, 267 mg, 0.81 mmol) in toluene (5 ml), N,N'-dimethylethylenediamine (DMEDA, 85 mg, 0.97 mmol) and triethylaluminum (2.6 ml, 2.64 mmol, 1 M in hexane) were reacted to give the title compound as a yellow solid.

$^1$H NMR (300 MHz, $CDCl_3$) δ 1.25 (t, J=7.33 Hz, 3H), 3.35 (q, J=7.13 Hz, 2H), 7.16-7.24 (m, 2H), 7.28-7.32 (m, 6H), 7.38-7.46 (m, 2H), 7.85 (d, J=7.92 Hz, 1H), 8.05 (d, J=7.92 Hz, 1H).

Example 77

1-[6-Phenyl-5-(4-trifluoromethyl-phenyl)-pyridin-2-yl]-ethanone (Compound 77). Following General Procedure O, 6-phenyl-5-(4-trifluoromethyl-phenyl)-pyridine-2-carboxylic acid ethyl ester (Compound 25, 49 mg, 0.13 mmol) in toluene (3 ml), N,N'-dimethylethylenediamine (DMEDA, 13 mg, 0.15 mmol) and trimethylaluminum (0.2 ml, 2.64 mmol, 2 M in toluene) were reacted to produce the title compound as a yellow oil.

$^1$H NMR (300 MHz, $CDCl_3$) δ 2.80 (s, 3H), 7.12-7.23 (m, 2H), 7.28-7.38 (m, 3H), 7.47-7.62 (m, 4H), 7.89 (d, J=7.92 Hz, 1H), 8.11 (d, J=7.92 Hz, 1H).

Example 78

1-[6-Phenyl-5-(4-trifluoromethyl-phenyl)-pyridin-2-yl]-propan-1-one (Compound 78). Following General Procedure O, 6-phenyl-5-(4-trifluoromethyl-phenyl)-pyridine-2-carboxylic acid ethyl ester (Compound 25, 94 mg, 0.25 mmol) in toluene (3 ml), N,N'-dimethylethylenediamine (DMEDA, 25 mg, 0.28 mmol) and triethylaluminum (0.7 ml, 0.76 mmol, 1 M in hexane) were reacted to produce the title compound as a oil.

$^1$H NMR (300 MHz, $CDCl_3$) δ 1.25 (t, J=7.18 Hz, 3H), 3.33 (q, J=7.33 Hz, 2H), 7.15-7.24 (m, 2H), 7.28-7.40 (m, 3H), 7.45-7.62 (m, 4H), 7.88 (d, J=7.92 Hz, 1H), 8.10 (dd, J=8.06, 1.91 Hz, 1H).

Example 79

1-[5-Phenyl-6-(4-trifluoromethyl-phenyl)-pyridin-2-yl]-propan-1-one (Compound 79). Following General Procedure O, 5-phenyl-6-(4-trifluoromethyl-phenyl)-pyridine-2-carboxylic acid ethyl ester (Compound 29, 292 mg, 0.71 mmol) in toluene (5 ml), N,N'-dimethylethylenediamine (DMEDA, 76 mg, 0.86 mmol) and triethylaluminum (2.4 ml, 0.35 mmol, 1 M in hexane) were reacted to produce the title compound as a oil.

$^1$H NMR (300 MHz, $CDCl_3$) δ 1.25 (t, J=7.18 Hz, 3H), 3.35 (q, J=7.33 Hz, 2H), 7.27-7.43 (m, 7H), 7.56 (d, J=8.21 Hz, 2H), 7.84 (d, J=7.92 Hz, 1H), 8.08 (d, J=7.92 Hz, 1H).

Example 80

1-(5,6-Diphenyl-pyridin-2-yl)-ethanone Oxime (Compound 80). General Procedure P. 1-(5,6-Diphenyl-pyridin-2-yl)-ethanone (Compound 75, 119 mg, 0.44 mmol), $NH_2OH$—HCl (103 mg, 1.48 mmol) and pyridine (272 mg, 0.27 mmol) was dissolved in EtOH (2 ml), and the mixture was heated to 70° C. under nitrogen for 3 hours. The reaction was quenched with water, and the product was extracted with ethyl acetate. The combined organic layers were washed with brine, and dried over $Na_2SO_4$. The filtered solvents were concentrated in vacuo, and the residue was purified by silica gel chromatography (15% ethyl acetate in hexane) to give title compound as an oil.

¹H NMR (300 MHz, CDCl₃) δ 2.47 (s, 3H), 7.12-7.36 (m, 8H), 7.35-7.49 (m, 2H), 7.71 (d, J=7.92 Hz, 1H), 7.87 (d, J=8.21 Hz, 1H).

Example 81

1-(5,6-Diphenyl-pyridin-2-yl)-propan-1-one Oxime (Compound 81). Following General Procedure P, 1-(5,6-diphenyl-pyridin-2-yl)-propan-1-one (Compound 76, 90 mg, 0.31 mmol), NH₂OH—HCl (87 mg, 1.25 mmol) and pyridine (272 mg, 0.27 mmol) in EtOH (2 ml) were reacted to give title compound as a white solid.

¹H NMR (300 MHz, CDCl₃) δ 1.24 (t, J=7.48 Hz, 3H), 3.08 (q, J=7.52 Hz, 2H), 7.13-7.35 (m, 8H), 7.35-7.46 (m, 2H), 7.70 (d, J=8.21 Hz, 1H), 7.84 (d, J=7.92 Hz, 1H).

Example 82

1-(5,6-Diphenyl-pyridin-2-yl)-ethanone O-Methyloxime (Compound 82). General Procedure Q. To a suspension of NaH (20 mg, 0.80 mmol) in THF (2 ml) at 0° C. was added a solution of 1-(5,6-diphenyl-pyridin-2-yl)-ethanone oxime (Compound 80, 46 mg, 0.16 mmol) in THF (1 ml). After the mixture was stirred at the same temperature for 1 hour, MeI (140 mg, 0.99 mmol) was added and the solution was stirred overnight at room temperature. The reaction was quenched with water, and the products were extracted with ethyl acetate. The combined organic layers were washed with brine and dried over Na₂SO₄. The filtered solvent was concentrated in vacuo, and the residue was purified by silica gel chromatography (10% ethyl acetate in hexane) to give title compound as an oil.

¹H NMR (300 MHz, CDCl₃) δ 2.40 (s, 3H), 4.06 (s, 3H), 7.11-7.34 (m, 8H), 7.37-7.45 (m, 2H), 7.69 (d, J=7.92 Hz, 1H), 7.94 (d, J=8.21 Hz, 1H).

Example 83

1-(5,6-Diphenyl-pyridin-2-yl)-propan-1-one O-Methyloxime (Compound 83). Following General Procedure Q, 1-(5,6-diphenyl-pyridin-2-yl)-propan-1-one oxime (Compound 81, 30 mg, 0.1 mmol), NaH (4.8 mg, 0.20 mmol) and MeI (140 mg, 0.99 mmol) in THF were reacted to obtain the title compound as an oil.

¹H NMR (300 MHz, CDCl₃) δ 1.19 (t, J=7.62 Hz, 3H), 3.01 (q, J=7.62 Hz, 2H), 4.04 (s, 3H), 7.13-7.32 (m, 8H), 7.37-7.45 (m, 2H), 7.69 (d, J=7.92 Hz, 1H), 7.90 (d, J=8.21 Hz, 1H).

Example 84

1-[6-Phenyl-5-(4-trifluoromethyl-phenyl)-pyridin-2-yl]-ethanone O-Methyl-oxime (Compound 84). Following General Procedure P, 1-[6-phenyl-5-(4-trifluoromethyl-phenyl)-pyridin-2-yl]-ethanone (Compound 77, 15 mg, 0.04 mmol), NH₂OMe—HCl (15 mg, 0.18 mmol) and pyridine (14 mg, 0.18 mmol) in EtOH (2 ml) were reacted to give title compound as a white solid. (12 mg, 75%).

¹H NMR (300 MHz, CDCl₃) δ 2.40 (s, 3H), 4.07 (s, 3H), 7.12-7.24 (m, 2H), 7.28-7.36 (m, 3H), 7.44-7.61 (m, 4H), 7.73 (d, J=7.92 Hz, 1H), 8.00 (d, J=8.21 Hz, 1H).

Example 85

1-[6-Phenyl-5-(4-trifluoromethyl-phenyl)-pyridin-2-yl]-propan-1-one O-Methyloxime (Compound 85). Following General Procedure P, 1-[6-phenyl-5-(4-trifluoromethyl-phenyl)-pyridin-2-yl]-propan-1-one (Compound 78, (24 mg, 0.07 mmol), NH₂OMe—HCl (23 mg, 0.25 mmol) and pyridine (21 mg, 0.28 mmol) in EtOH (2 ml) were reacted to give title compound as a white solid.

¹H NMR (300 MHz, CDCl₃) δ 1.19 (t, J=7.48 Hz, 3H), 2.99 (q, J=7.62 Hz, 2H), 4.04 (s, 3H), 7.12-7.22 (m, 2H), 7.27-7.37 (m, 3H), 7.43-7.56 (m, 4H), 7.72 (d, J=7.92 Hz, 1H), 7.96 (d, J=8.21 Hz, 1H).

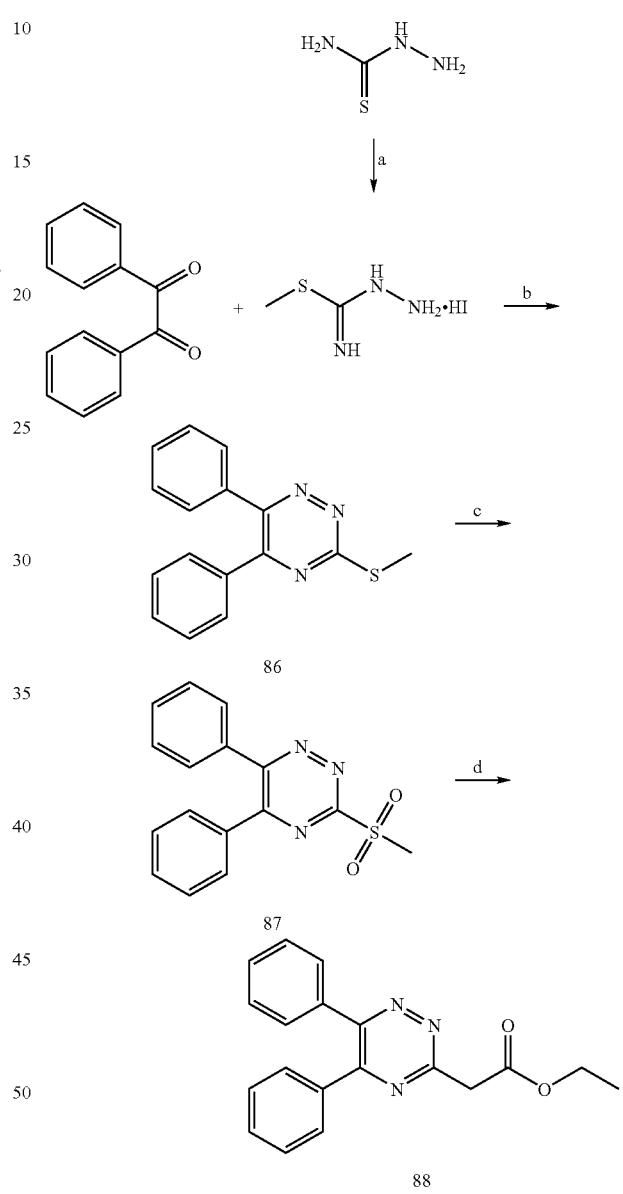

(a) MeI, EtOH, 60° C., 30 min; (b) EtOH, rt; (c) mCPBA, CH₂Cl₂; acetoacetic acid ethyl ester, NaH, THF.

Example 86

3-(Methylthio)-5,6-diphenyl-1,2,4-triazine (86). To a solution of thiosemicarbazide (1 g, 10.97 mmol) in ethanol (10 ml) was added MeI (1.6 g, 10.97 mmol). After the suspension was heated at 60° C. for 30 min., the mixture was cooled and concentrated in vacuo to remove solvent. The solid was filtered and washed with ether to produce S-methyl isothiosemicarbazide hydroiodide as a yellow solid (2.5 g, 98%). To the suspension solution of benzyl (1.4 g, 6.46 mmol) in ethanol (20 ml) was added the pre-made S-methyl isothiosemicarbazide hydroiodide (1 g, 4.29 mmol) in one portion. After stirring at room temperature overnight, the reaction was quenched by adding NaHCO₃ and Na₂S₂O₃ and stirring for 30 min. The mixture was filtered, and the solvent was removed in vacuo, and the residue was purified by column chromatography (15% ethyl acetate in hexane) to give title compound as a yellow solid.

¹H NMR (300 MHz, CDCl₃) δ 2.77 (s, 3H), 7.28-7.47 (m, 6H), 7.48-7.60 (m, 4H).

Example 87

3-(Methylsulfonyl)-5,6-diphenyl-1,2,4-triazine (87). General Procedure R. To a stirred solution of 3-(methylthio)-5,6-diphenyl-1,2,4-triazine (Compound 86) (858 mg, 3.08 mmol) in anhydrous CH₂Cl₂ (50 ml) at 0° C. was added a suspension of m-chloroperbenzoic acid (2.1 g, 6.16 mmol) in anhydrous CH₂Cl₂ (50 ml). After one hour, the reaction was quenched with Na₂SO₃ (aq.). The organic layer was washed with water, and brine, and dried over Na₂SO₄. The filtered solvents were concentrated in vacuo, and the residue was purified by column chromatography (20% ethyl acetate in hexane) to give title compound as a solid.

¹H NMR (300 MHz, CDCl₃) δ 3.57 (s, 3H), 7.32-7.56 (m, 6H), 7.58-7.70 (m, 4H)

Example 88

Ethyl 2-(5,6-Diphenyl-1,2,4-triazin-3-yl)acetate (88). To a suspension of NaH (41 mg, 1.61 mmol) in THF (2 ml) at 0° C. was added ethyl acetoacetate (105 mg. 0.80 mmol) dropwise. After the mixture was stirred for 15 min, a solution of 3-(methylsulfonyl)-5,6-diphenyl-1,2,4-triazine (Compound 87) (250 mg, 0.80 mmol) in THF (3 ml) was cannulated into the solution, and the resulting solution was heated to 60° C. for 2 hours. The reaction was then quenched with water. The product was extracted with ethyl acetate. The organic layer was washed with water, and brine, and dried over Na₂SO₄. The filtered solvent was concentrated in vacuo, and the residue was purified by silica gel chromatography (20% ethyl acetate in hexane) to give title compound as a solid.

¹H NMR (300 MHz, CDCl₃) δ 1.31 (t, J=7.04 Hz, 3H), 4.21-4.32 (m, 4H), 7.29-7.47 (m, 6H), 7.52-7.59 (m, 4H).

Example 89

Methyl 6-(4-Ethyl-phenyl)-5-phenyl-1,2,4-triazine-3-carboxylate (89). Following General Procedure E, ethyl 6-(4-ethyl-phenyl)-5-phenyl-1,2,4-triazine-3-carboxylic acid (Compound 13, 6 mg, 0.018 mmol) was converted to the title compound.

1H NMR (300 MHz, CDCl₃) δ ppm 1.26 (t, J=7.62 Hz, 3H), 2.69 (q, J=7.72 Hz, 2H), 4.14 (s, 3H) 7.22 (d, J=8.50 Hz, 2H), 7.32-7.41 (m, 2H), 7.43-7.51 (m, 1H), 7.55 (d, J=8.21 Hz, 2H), 7.62-7.70 (m, 2H).

Example 90

(5,6-diphenylpyridin-2-yl)methanol (90), as AGN-210851. Following General Procedure L, ethyl 5,6-diphenylpyridine-2-carboxylate (Compound 21, 145 mg, 0.48 mmol) was converted to the title compound.

¹H NMR (300 MHz, CDCl₃) δ ppm 4.76 (s, 2H), 7.07-7.17 (m, 2H), 7.18-7.22 (m, 7H), 7.27-7.31 (m, 2H), 7.64 (d, J=7.91 Hz, 1H).

Example 91

5,6-Diphenyl-pyridine-2-carboxylic acid (91). A solution of ethyl 5,6-diphenylpyridine-2-carboxylate (Compound 21, 40 mg, 0.13 mmol) and LiOH (1N, 1 ml) in EtOH (2 ml) was stirred at room temperature overnight. The mixture was acidified with 10% HCl, then extracted with EtOAc. The organic layer was washed with water, and brine, and dried over Na₂SO₄. The filtered solvent was concentrated in vacuo, and the residue was purified by silica gel chromatography (20-80% Ethyl acetate in hexane) to give title compound as a solid.

¹H NMR (300 MHz, CDCl₃) δ 7.17-7.21 (m, 2H), 7.26-7.37 (m, 8H), 7.97 (d, J=7.62 Hz, 1H), 8.23 (d, J=7.92 Hz, 1H).

Example 92

6-Methoxymethyl-2,3-diphenyl-pyridine (92). A solution of 5,6-diphenylpyridin-2-yl)methanol (Compound 90, 15 mg, 0.06 mmol), MeI (0.1 ml), K₂CO₃ (50 mg) and KOH (5N, 5 drops) in acetone was heated at 56° C. over night. The mixture was diluted with water and the product was extracted with ethyl acetate. The organic layer was washed with water, and brine, and dried over Na₂SO₄. The filtered solvent was concentrated in vacuo, and the residue was purified by silica gel chromatography (15% ethyl acetate in hexane) to give title compound as a solid.

¹H NMR (300 MHz, CDCl₃) δ 3.54 (s, 3H), 4.71 (s, 2H), 7.14-7.18 (m, 2H), 7.22-7.27 (m, 6H), 7.33-7.36 (m, 2H), 7.47 (d, J=7.92 Hz, 1H), 7.74 (d, J=7.92 Hz, 1H).

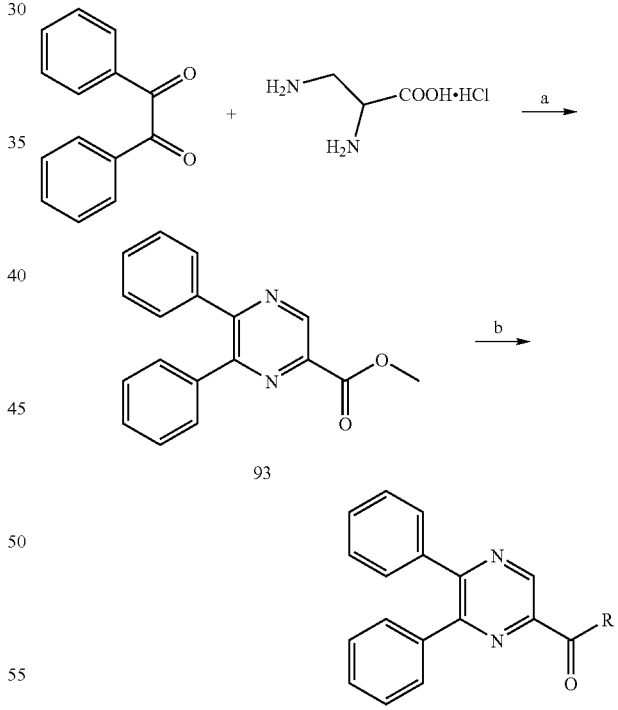

Scheme 7

94, R = Me
95, R = Et (a) i) NaOH, MeOH, 69° C., 6 hrs, ii) c. H₂SO₄, MeOH, 69° C., 3 hrs.; (b) Me₃Al, or Et₃Al, DMEDA, toluene, 110° C., 3 hrs.

Example 93

Methyl 5,6-Diphenyl-pyrazine-2-carboxylate (93). To a solution of benzyl (500 mg, 2.38 mmol) and 2,3-diaminoproprionic acid monohydro chloride (334 mg, 2.38 mmol) in MeOH (10 ml) was added NaOH (380 mg, 9.51 mmol) at room temperature. After the mixture was refluxed for 6 hours, it was cooled down in an ice-bath, conc. $H_2SO_4$ (1 ml) was added dropwise and the whole mixture was stirred under reflux for 3 hours. MeOH was removed and the residue was dissolved in water, extracted with ethyl acetate. The organic layer was washed with $NaHCO_3$ (sat.), water, and brine, dried over $Na_2SO_4$, concentrated in vacuo and purified by column chromatography (15% ethyl acetate in hexane) to give the title compound as a yellow solid.

$^1$H NMR (300 MHz, $CDCl_3$) δ ppm 4.06 (s, 3H), 7.27-7.40 (m, 6H), 7.45-7.54 (m, 4H), 9.28 (s, 1H).

Example 94

1-(5,6-Diphenyl-pyrazin-2-yl)-ethanone (94). Following General Procedure O, methyl 5,6-diphenyl-pyrazine-2-carboxylate (Compound 93, 83 mg, 0.29 mmol), $Me_3Al$ (0.4 ml, 2M in toluene), DMEDA (28 mg, 0.32 mmol) in toluene was reacted to afford the title compound.

$^1$H NMR (300 MHz, $CDCl_3$) δ 2.80 (s, 3H), 7.31-7.42 (m, 6H), 7.47-7.56 (m, 4H), 9.21 (s, 1H).

Example 95

1-(5,6-Diphenyl-pyrazin-2-yl)-propan-1-one (95). Following General Procedure O, methyl 5,6-diphenyl-pyrazine-2-carboxylate (Compound 93) (92 mg, 0.32 mmol), $Et_3Al$ (0.9 ml, 1M in hexane), DMEDA (38 mg, 0.35 mmol) in toluene was reacted to afford the title compound.

$^1$H NMR (300 MHz, $CDCl_3$) δ 1.26 (t, J=7.33 Hz, 3H), 3.31 (q, J=7.33 Hz, 2H), 7.28-7.42 (m, 6H), 7.45-7.56 (m, 4H), 9.20 (s, 1H).

Scheme 8

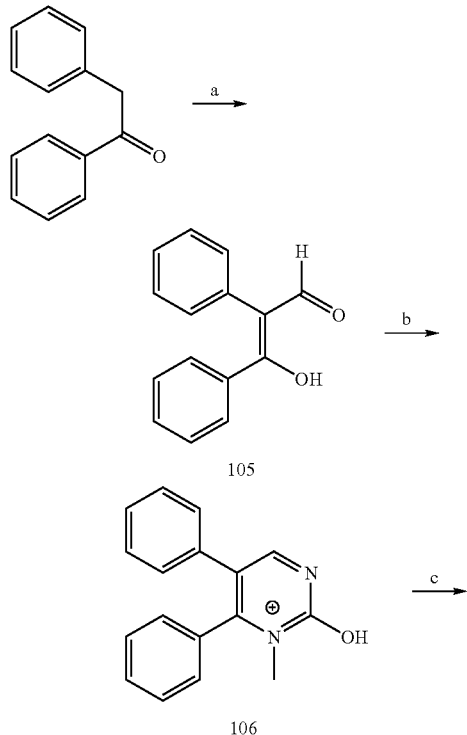

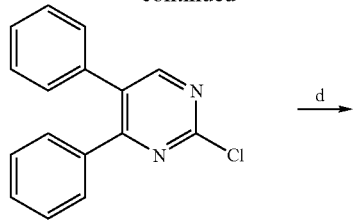

107

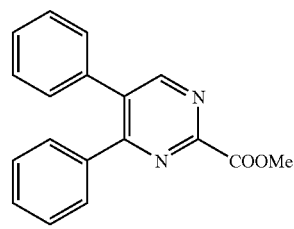

96

(a) NaOEt, ethyl formate, EtOH, 0° C. to rt; (b) pTSA, methyl urea, toluene, 110° C., 12 hr; (c) $PCl_5$, $POCl_3$, 120° C., 3 hrs; (d) CO(g), dppf, Pd(OAc)$_2$, $CH_3COONa$, MeOH, THF, sealed-tube, 110° C.

Example 105

(Z)-3-Hydroxy-2,3-diphenyl-propenal (105). To a cooled solution of NaOEt (763 mg, 11.21 mmol) in EtOH (100 ml) was added ethyl formate (0.91 ml, 11.21 mmol) dropwise. The resulting mixture is allowed to stand for 3 hours at 0 to 5° C., and then deoxybenzoin (2 g, 10.19 mmol) was added. The mixture was stirred for 2 hours at 0 to 5° C. and then placed in the refrigerator for 4 days. After the mixture was stirred overnight at room temperature, it was poured into ice-water, and acidified, and extracted with $CH_2Cl_2$. The organic layer was washed with brine, and dried over $MgSO_4$ anhydride, and concentrated in vacuo. The residue was purified by column chromatography (10% ethyl acetate in hexane) to give the title compound as a light yellow solid.

$^1$H NMR (500 MHz, $CDCl_3$) δ ppm 7.12-7.23 (m, 2H), 7.26-7.40 (m, 5H), 7.41-7.50 (m, 3H), 8.73 (d, J=5.37 Hz, 1H).

Example 106

1-Methyl-5,6-diphenyl-1H-pyrimidin-2-one (106). A solution of (Z)-3-hydroxy-2,3-diphenyl-propenal (105, 423 mg, 1.89 mmol), pTSA (30 mg, 7.56 mmol) and methyl urea (118 mg, 0.62 mmol) in toluene was heated at 110° C. overnight. The reaction was quenched with water, and the products were extracted with ethyl acetate. The organic layer was separated and washed with brine, and dried over $MgSO_4$, and concentrated in vacuo to produce a yellow oil. The crude product was dissolved in $CH_2Cl_2$ and titrated with diethyl ether to give the title compound as a white solid.

$^1$H NMR (500 MHz, $CDCl_3$) δ ppm 3.32 (s, 3H), 6.88-7.12 (m, 2H), 7.07-7.25 (m, 3H), 7.31-7.40 (m, 2H), 7.39-7.48 (m, 3H), 8.58 (s, 1H).

Example 107

2-Chloro-4,5-diphenyl-pyrimidine (107). A solution of 1-methyl-5,6-diphenyl-1H-pyrimidin-2-one (106, 314 mg, 1.20 mmol), phosphorus oxychloride (0.6 ml, 6.4 mmol) and phosphorus pentachloride (55 mg, 0.26 mmol) was heated at 120° C. for 3 hours. The excess amount of phosphorus oxychloride was removed under reduced pressure and cold water was added to the residue. The resulting precipitate was extracted with CH$_2$Cl$_2$. The organic layer was washed with brine, and dried over MgSO$_4$, and concentrated in vacuo. The residue was purified by column chromatography (20% ethyl acetate in hexane) to produce the title compound as a white solid.

$^1$H NMR (500 MHz, CDCl$_3$) δ ppm 7.16-7.23 (m, 2H), 7.24-7.32 (m, 3H), 7.33-7.40 (m, 3H), 7.42-7.47 (m, 2H), 8.59 (s, 1H).

Example 96

Methyl 4,5-Diphenyl-pyrimidine-2-carboxylate (96). A solution of 2-chloro-4,5-diphenyl-pyrimidine (107, 203 mg, 0.76 mmol) and sodium acetate (188 mg, 2.21 mmol) in MeOH (6 ml) and THF (2 ml) was degassed under argon for 10 min. Pd(OAc)$_2$ (2.1 mg) and DPPF (13 mg) were added and CO (g) was bubbled through the solution. The reaction was heated to 110° C. in a sealed tube for 2 days. The solvent was removed in vacuo and the crude product was purified by column chromatography (10% ethyl acetate in hexane) to get the title compound.

$^1$H NMR (500 MHz, CDCl$_3$) δ ppm 4.14 (s, 3H), 7.16-7.23 (m, 2H), 7.29 (d, J=7.32 Hz, 2H), 7.32-7.39 (m, 4H), 7.49 (d, J=7.32 Hz, 2H), 8.54 (s, 1H).

J=7.16 Hz, 2H), 7.01 (d, J=8.30 Hz, 2H), 7.05 (d, J=8.30 Hz, 2H), 7.29-7.31 (m, 4H), 7.35 (d, J=7.81 Hz, 1H), 7.56 (d, J=7.81 Hz, 1H).

Example 97

Methyl 5-(4-Ethyl-phenyl)-1-hydroxy-6-phenyl-pyridine-2-carboxylate, N-Oxide (97).

Following General Procedure E, 5-(4-ethyl-phenyl)-1-hydroxy-6-phenyl-pyridine-2-carboxylate, N-oxide (108, 6 mg, 0.017 mmol), c. H$_2$SO$_4$ (1 drop) in MeOH was reacted to afford the title compound.

$^1$H NMR (500 MHz, CDCl$_3$) δ ppm 1.18 (t, J=7.57 Hz, 3H), 2.58 (q, J=7.32 Hz, 2H), 4.00 (s, 3H), 6.94-7.00 (m, 2H), 7.00-7.06 (m, 2H), 7.27 (s, 4H), 7.32 (d, J=9.28 Hz, 1H), 7.56 (d, J=8.30 Hz, 1H).

Scheme 9

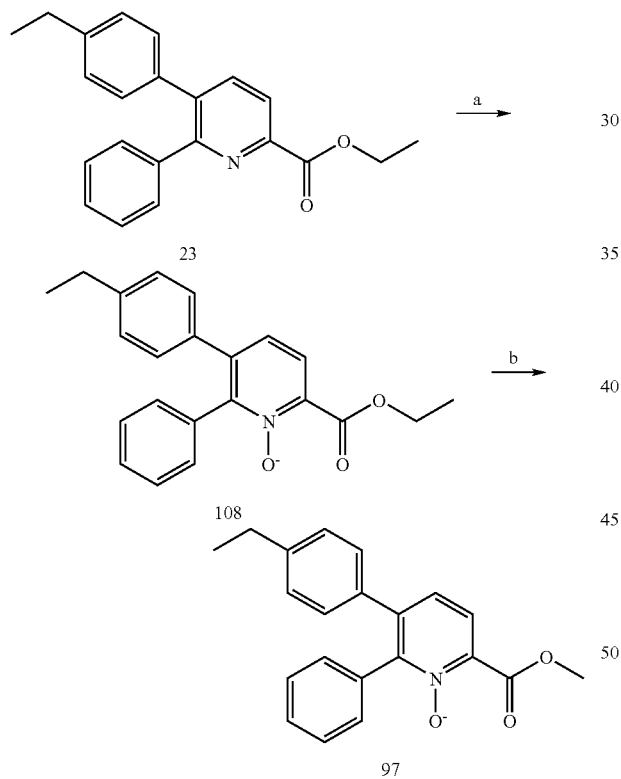

(a) mCPBA, CHCl$_3$, 5 days; (b) c•H$_2$SO$_4$, MeOH.

Example 108

Ethyl 5-(4-Ethyl-phenyl)-1-hydroxy-6-phenyl-pyridine-2-carboxylate, N-Oxide (108). Following General Procedure R, a solution of ethyl 5-(4-ethyl-phenyl)-6-phenyl-pyridine-2-carboxylate (23, 25 mg, 0.076 mmol), m-chloroperbenzoic acid (85 mg, 0.38 mmol) and anhydrous CHCl$_3$ (3 ml) was stirred at room temperature for 7 days to give title compound.

$^1$H NMR (500 MHz, CDCl$_3$) δ ppm 1.21 (t, J=7.57 Hz, 3H), 1.45 (t, J=7.08 Hz, 3H), 2.61 (q, J=7.81 Hz, 2H), 4.51 (q, Scheme 10

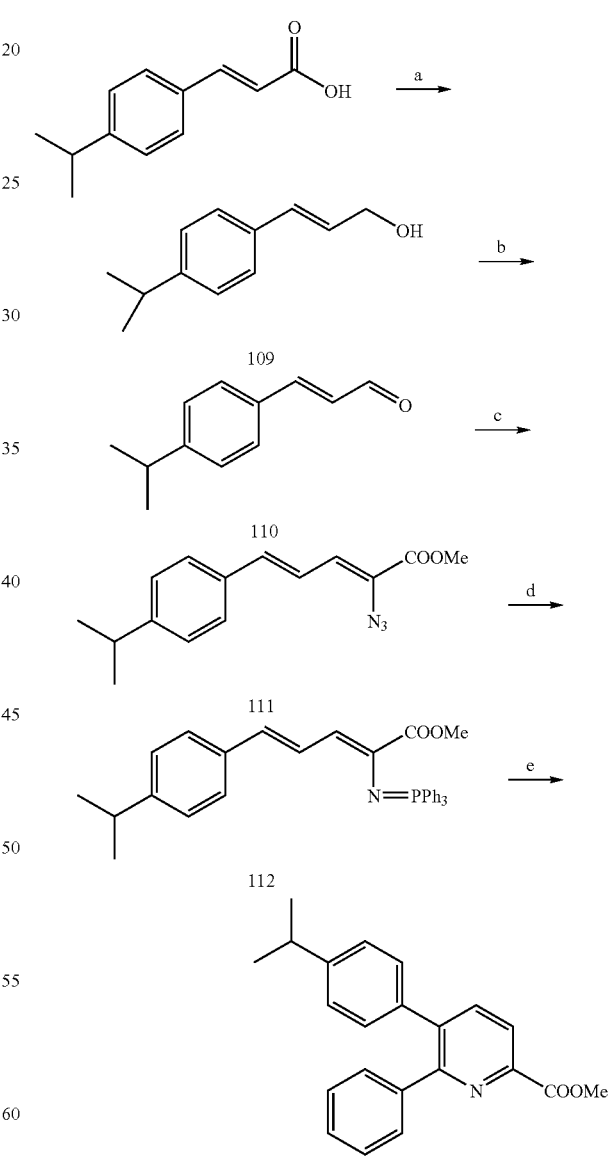

(a) i) Ethyl chloroformate, TEA, THF, ii) NaBH$_4$, H$_2$O, THF; (b)(COCl)$_2$, DMSO, TEA, -60° C.; (c) ethyl azidoacetate, NaOMe, MeOH; (d) PPh$_3$, ether; (e) PhCHO, CH$_3$CN, 60° C.

Example 109

(E)-3-(4-Isopropylphenyl)prop-2-en-1-ol (Compound 109). Following General Procedure G, 4-iso-propylcinnamic acid (3 g, 15.8 mmol), ethyl chloroformate (1.6 ml, 15.8 mmol) and triethylamine (2.2 ml, 15.8 mmol) in THF (100 ml) were reacted to produce a mixed anhydride, which was then were reacted with NaBH$_4$ (1.3 g, 34.7 mmol) in H$_2$O (30 ml) to produce title compound as a white solid.

$^1$H NMR (300 MHz, CDCl$_3$) δ ppm 1.26 (d, J=7.04 Hz, 6H), 2.86-2.97 (m, 1H), 4.32 (dd, J=5.86, 1.17 Hz, 2H), 6.29-6.38 (m, 1H), 6.61 (d, J=16.12 Hz, 1H), 7.16-7.24 (d, J=8.21 Hz, 2H), 7.33 (d, J=8.21 Hz, 2H)

Example 110

(E)-3-(4-Isopropylphenyl)acrylaldehyde (Compound 110). Following General Procedure H, oxalyl chloride (9.5 ml, 19.0 mmol, 2M in CH$_2$Cl$_2$), DMSO (1.8 ml, 25.3 mmol), (E)-3-(4-isopropylphenyl)prop-2-en-1-ol (Compound 109, 2.2 g, 12.6 mmol) and triethylamine (7.1 ml, 50.7 mmol) in CH$_2$Cl$_2$ (100 ml) were reacted to obtain the title compound as an oil.

$^1$H NMR (300 MHz, CDCl$_3$) δ ppm 1.28 (d, J=7.04 Hz, 6H), 2.77-3.11 (m, 1H), 6.70 (dd, J=15.83, 7.62 Hz, 1H), 7.31 (d, J=8.21 Hz, 1H), 7.45-7.59 (m, 3H), 9.70 (d, J=7.62 Hz, 1H)

Example 111

Methyl (2Z,4E)-2-Azido-5-(4-isopropylphenyl)penta-2,4-dienoate (Compound 111). Following General Procedure I, a 1.34 M solution of NaOMe in methanol (30 ml), (E)-3-(4-isopropylphenyl)acrylaldehyde (Compound 110, 1.4 g, 8.0 mmol) and ethyl azidoacetate (12 ml, 40.2 mmol) in MeOH (20 ml) were reacted to produce the title compound as a solid.

$^1$H NMR (300 MHz, CDCl$_3$) δ ppm 1.26 (d, J=6.74 Hz, 6H), 2.80-3.02 (m, 1H), 3.88 (s, 3H), 6.70-6.87 (m, 2H), 7.13 (dd, J=15.54, 11.43 Hz, 1H), 7.22 (d, J=8.21 Hz, 2H), 7.43 (d, 2H)

Example 112

3-Methoxycarbonyl-1,1,1-triphenyl-6-(4-isopropylphenyl)-2-aza-1λ$^5$-phosphahexa-1,3,5-triene (Compound 112). Following General Procedure J, triphenylphosphine (1.4 g, 5.2 mmol), methyl (2Z,4E)-2-azido-5-(4-isopropylphenyl) penta-2,4-dienoate (Compound 111, 1.4 g, 5.2 mmol) in diethyl ether (50 ml) were reacted to produce the title compound as a yellow solid.

$^1$H NMR (300 MHz, CDCl$_3$) δ ppm 1.26 (d, J=6.74 Hz, 6H), 2.81-2.98 (m, 1H), 3.44 (s, 3H), 6.58-6.76 (m, 2H), 7.15 (d, J=8.21 Hz, 2H), 7.32 (d, J=8.50 Hz, 2H), 7.37-7.57 (m, 9H), 7.76 (ddd, J=12.09, 7.99, 1.32 Hz, 7H)

Example 98

Methyl 5-(4-Isopropyl-phenyl)-6-phenyl-pyridine-2-carboxylate (Compound 98). Following General Procedure K, Benzaldehyde (0.48 g, 4.6 mmol) and 3-Methoxycarbonyl-1,1,1-triphenyl-6-(4-isopropylphenyl)-2-aza-1λ$^5$-phosphahexa-1,3,5-triene (Compound 112, 2.3 g, 4.6 mmol) in dry acetonitrile (100 ml) were reacted to produce the title compound as a yellow solid.

$^1$H NMR (300 MHz, CDCl$_3$) δ ppm 1.25 (d, J=7.04 Hz, 6H), 2.78-3.00 (m, 1H), 4.03 (s, 3H), 7.06-7.19 (m, 4H), 7.21-7.32 (m, 3H), 7.35-7.46 (m, 2H), 7.86 (d, J=7.92 Hz, 1H), 8.14 (d, J=7.92, 1H)

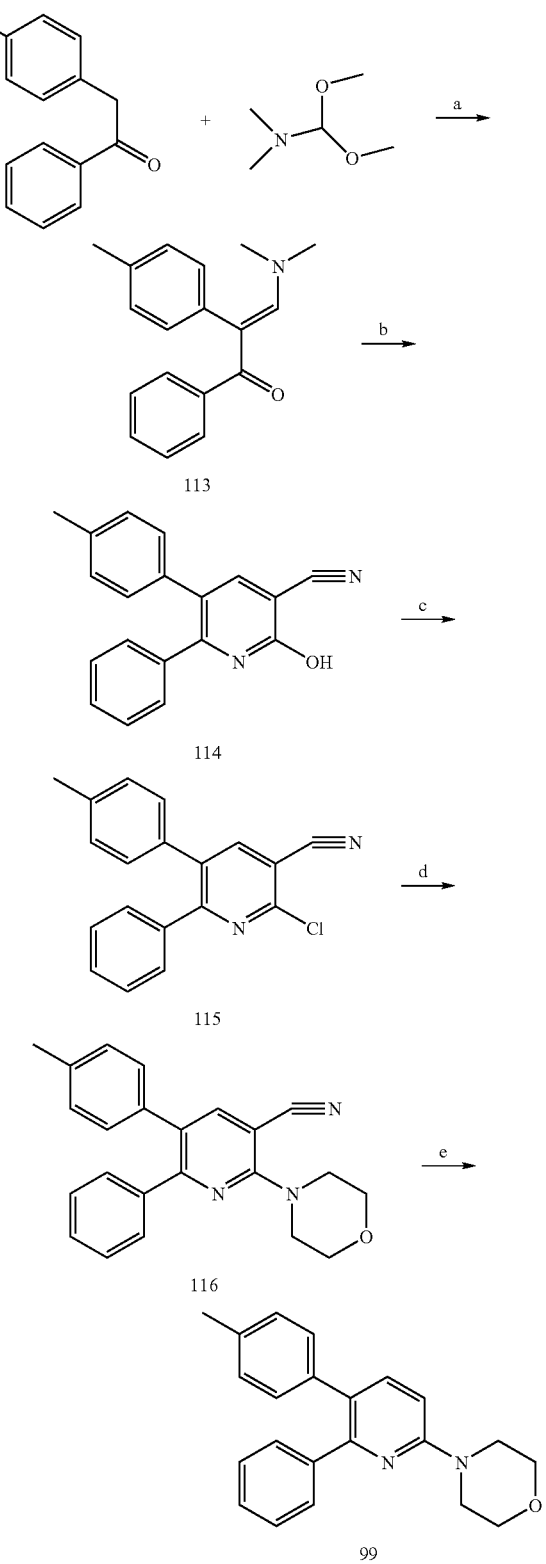

Scheme 11.

(a) DMF, 75° C., 24 hours; (b) NaH, cyanoacetamide, DMF, MeOH, 95° C. 2 hours; (c) POCl$_3$, 110° C.; (d) morpholine, DMF, 150° C., 2 hours; (e) 50% H$_2$SO$_4$, 140° C., overnight.

Example 113

(E)-3-(Dimethylamino)-1-phenyl-2-p-tolylprop-2-en-1-one (Compound 113). A solution of 1-phenyl-2-p-tolylethanone (2 g, 9.5 mmol) and dimethylformamide dimethylacetal (4.5 g, 38.1 mmol) in DMF (30 ml) was heated at 75° C. for 24 hours. Solvents were removed under high vacuum to obtain the title compound as a yellow oil, which was used directly in the next step without purification.

$^1$H NMR (300 MHz, CDCl$_3$) δ ppm 2.32 (s, 3H), 2.73 (s, 6H), 7.06 (s, 4H), 7.21-7.36 (m, 4H), 7.44 (d, 2H)

Example 114

2-Hydroxy-6-phenyl-5-p-tolylnicotinonitrile (Compound 114). A solution of (E)-3-(dimethylamino)-1-phenyl-2-p-tolylprop-2-en-1-one (Compound 113, 500 mg, 1.9 mmol), cyanoacetamide (175 mg, 2.1 mmol) and MeOH (0.2 ml, 2.2 mmol) in DMF (4 ml) was cannulated into a suspension of NaH (119 mg, 4.7 mmol, 95% in mineral oil) in DMF (2 ml) at room temperature. After the addition was completed, the reaction was heated to 95° C. for 2 hours. The reaction was quenched with water and extracted with ethyl acetate. The organic layer was washed with water and brine, dried over MgSO$_4$, concentrated in vacuo. The solid residue was triturated with diethyl ether, filtered and dried under high vacuum to yield the title compound as a white solid.

$^1$H NMR (300 MHz, CDCl$_3$) δ ppm 2.33 (s, 3H), 6.94 (d, J=8.21 Hz, 2H), 7.08 (d, J=7.92 Hz, 2H), 7.28-7.49 (m, 5H), 7.97 (s, 1H)

Example 115

2-Chloro-6-phenyl-5-p-tolylnicotinonitrile (Compound 115). A solution of 2-hydroxy-6-phenyl-5-p-tolylnicotinonitrile (Compound 114, 528 mg, 1.9 mmol) in POCl$_3$ (5 ml) was heated to 110° C. overnight. POCl$_3$ was removed and the residue was purified by MPLC column chromatography (silica gel, 10% ethyl acetate in hexane) to obtain the title compound as an oil-foam.

$^1$H NMR (300 MHz, CDCl$_3$) δ ppm 2.36 (s, 3H), 6.98-7.18 (m, 4H), 7.21-7.45 (m, 5H), 7.97 (s, 1H)

Example 116

2-Morpholino-6-phenyl-5-p-tolylnicotinonitrile (Compound 116). A solution of 2-chloro-6-phenyl-5-p-tolylnicotinonitrile (Compound 115, 124 mg, 0.4 mmol) and morpholine (36 mg, 0.4 mmol) in DMF (2 ml) was heated at 150° C. for 2 hours. The solvents was removed and the residue was purified by MPLC column chromatography (silica gel, 10% ethyl acetate in hexane) to obtain the title compound as a white solid.

$^1$H NMR (300 MHz, CDCl$_3$) δ ppm 2.34 (s, 3H), 3.77-3.94 (m, 8H), 6.95-7.14 (m, 4H), 7.18-7.34 (m, 3H), 7.34-7.43 (m, 2H), 7.82 (s, 1H)

Example 99

4-(6-Phenyl-5-p-tolylpyridin-2-yl)morpholine (Compound 99). A solution of 2-morpholino-6-phenyl-5-p-tolylnicotinonitrile (Compound 116,120 mg, 0.3 mmol) in 50% H$_2$SO$_4$ (5 ml) was heated at 140° C. overnight. The mixture was cooled down to room temperature and diluted with water, extracted with CH$_2$Cl$_2$. The organic layer was washed with water and brine, dried over MgSO$_4$, concentrated in vacuo and purified by MPLC column chromatography (silica gel, 25% ethyl acetate in hexane) to provide the title compound as a white solid.

$^1$H NMR (300 MHz, CDCl$_3$) δ ppm 2.34 (s, 3H), 3.63 (d, J=4.98 Hz, 4H), 3.86 (d, J=4.98 Hz, 4H), 6.68 (d, J=8.50 Hz, 1H), 7.05 (s, 4H), 7.19-7.26 (m, 3H), 7.41 (dd, J=6.89, 3.08 Hz, 2H), 7.57 (d, J=8.79 Hz, 1H)

While this invention has been described with respect to various specific examples and embodiments, it is to be understood that the invention is not limited thereto and that it can be variously practiced within the scope of the following claims. In particular, the present invention contemplates and includes a compound comprising a 6-membered heteroaromatic ring including one, two or three enchained nitrogen atoms at the 1, or 1 and 3 or 1, 3 and 4 positions, respectively, and the remaining ring atoms being carbon, an aryl radical directly bonded to said 6-membered heteroaromatic ring at both of the 5 and 6 positions and a side chain at the 2 position of said 6-membered heteroaromatic ring, wherein said side chain terminates with an end group selected from the group consisting of a phosphonic acid, a lower alkyl ester thereof, a carboxylic acid, a lower alkyl ester thereof, a lower alkyl ether and a lower alkylcarboxy and a compound comprising a 6-membered heteroaromatic ring including one, two or three enchained nitrogen atoms and the remaining ring atoms being carbon, an aryl radical directly bonded to said 6-membered heteroaromatic ring at both of the 5 and 6 positions and a side chain at the 2 position of said 6-membered heteroaromatic ring, wherein said side chain terminates with an end group selected from the group consisting of a phosphonic acid, a lower alkyl ester thereof, a carboxylic acid, a lower alkyl ester thereof, a lower alkyl ether and a lower alkylcarboxy.

What is claimed is:

1. A compound having agonist activity at the S1P$_3$ receptor, wherein said compound has a structure selected from

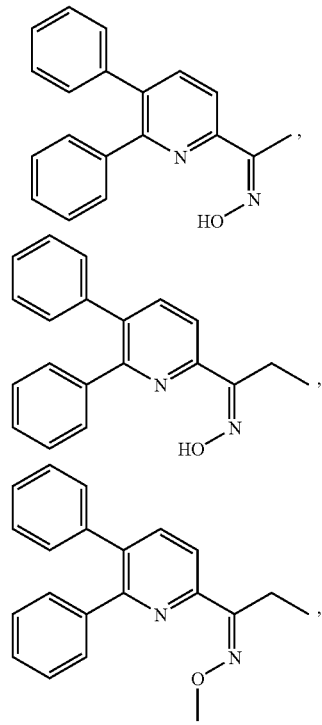

-continued
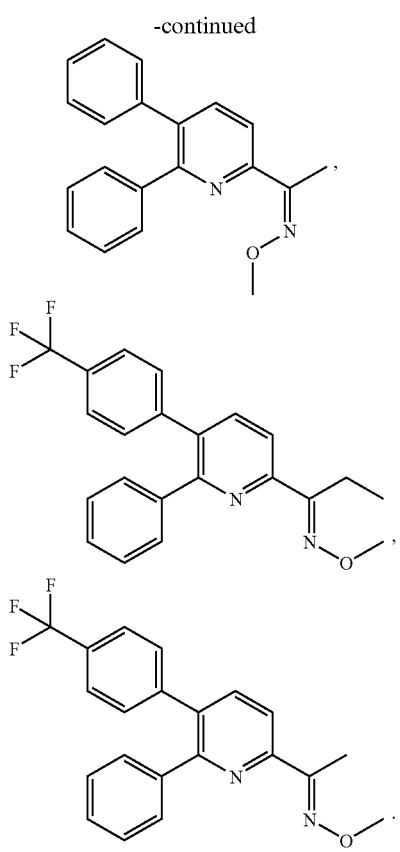
2. The compound according to claim 1 having the structure
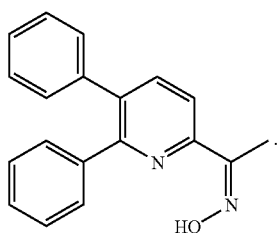
3. The compound according to claim 1 having the structure
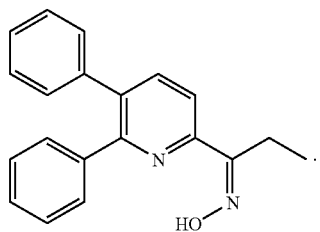
4. The compound according to claim 1 having the structure
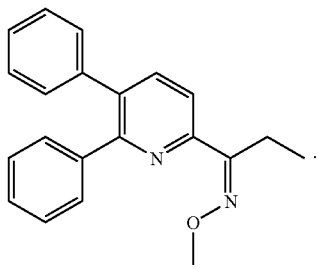
5. The compound according to claim 1 having the structure
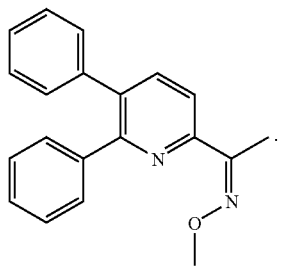
6. The compound according to claim 1 having the structure
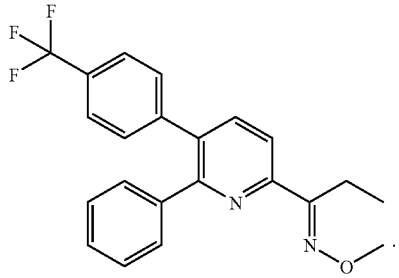
7. The compound according to claim 1 having the structure
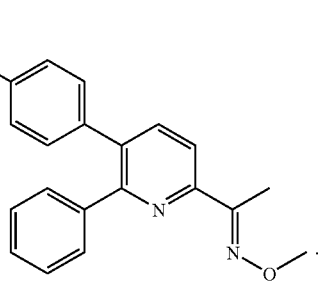
* * * * *

UNITED STATES PATENT AND TRADEMARK OFFICE
CERTIFICATE OF CORRECTION

PATENT NO. : 7,728,014 B2  Page 1 of 2
APPLICATION NO. : 11/850756
DATED : June 1, 2010
INVENTOR(S) : Richard L. Beard et al.

It is certified that error appears in the above-identified patent and that said Letters Patent is hereby corrected as shown below:

On the title page, item (56), in column 2, under "Other Publications", line 2, delete "Oquinoxalines" and insert -- Quinoxalines --, therefor.

On the title page, item (57), in column 2, in "Abstract", line 12, after "$NOR^4$" insert -- ; --.

In column 1, line 50, delete "sphingomeyeline" and insert -- sphingomyelin --, therefor.

In column 3, line 20, after "$NOR^4$" insert -- ; --.

In column 5, line 18, delete "Diels-Aler" and insert -- Diels-Alder --, therefor.

In column 6, line 32, delete "isooxazole," and insert -- isoxazole, --, therefor.

In column 6, line 52, delete "R1" and insert -- $R^1$ --, therefor.

In column 7, line 53, after "ethyl" insert -- . --.

In column 8, line 3, after "loweralkylthio" insert -- . --.

In column 10, line 34, delete "Levenburg" and insert -- Levenberg --, therefor.

In column 27, line 66, delete "hereof," and insert -- hereof; --, therefor.

In column 34, line 5, delete "3-carboxylatate" and insert -- 3-carboxylate --, therefor.

In column 46, line 23, before "3" insert -- ( --.

In column 47, line 11, delete "δ1.25" and insert -- δ 1.25 --, therefor.

In column 48, line 29, delete "δ1.20" and insert -- δ 1.20 --, therefor.

Signed and Sealed this

Nineteenth Day of October, 2010

David J. Kappos
*Director of the United States Patent and Trademark Office*

In column 53, line 25, after "4H)" insert -- . --.

In column 54, line 66-67, delete "2,3-diaminoproprionic" and insert -- 2,3-diaminopropionic --, therefor.

In column 59, line 13, after "2H)" insert -- . --.

In column 59, line 27, after "1H)" insert -- . --.

In column 59, line 39, after "2H)" insert -- . --.

In column 59, line 53, after "7H)" insert -- . --.

In column 59, line 67, after "1H)" insert -- . --.

In column 61, line 11, after "2H)" insert-- . --.

In column 61, line 30, after "1H)" insert -- . --.

In column 61, line 42, after "1H)" insert -- . --.

In column 61, line 57, after "1H)" insert --. --.

In column 62, line 7, after "1H)" insert --. --.